(12) United States Patent
Hernan et al.

(10) Patent No.: US 7,799,561 B2
(45) Date of Patent: Sep. 21, 2010

(54) AFFINITY PEPTIDES AND METHOD FOR PURIFICATION OF RECOMBINANT PROTEINS

(75) Inventors: Ronald A. Hernan, Ballwin, MO (US); Richard J. Mehigh, St. Louis, MO (US); Ian R. Brockie, St. Louis, MO (US); Elizabeth Jenkins, Sherman, IL (US)

(73) Assignee: Sigma-Aldrich, Co., St. Louis, MO (US)

( * ) Notice: Subject to any disclaimer, the term of this patent is extended or adjusted under 35 U.S.C. 154(b) by 930 days.

(21) Appl. No.: 10/460,524

(22) Filed: Jun. 12, 2003

(65) Prior Publication Data

US 2004/0029781 A1 Feb. 12, 2004

Related U.S. Application Data

(60) Provisional application No. 60/388,059, filed on Jun. 12, 2002.

(51) Int. Cl.
*C12N 15/63* (2006.01)
*C07K 5/00* (2006.01)
*C12N 15/00* (2006.01)
*C12N 15/85* (2006.01)

(52) U.S. Cl. .................. 435/320.1; 530/300; 435/69.7; 435/325

(58) Field of Classification Search ........................ None
See application file for complete search history.

(56) References Cited

U.S. PATENT DOCUMENTS

| | | | |
|---|---|---|---|
| 4,569,794 A | 2/1986 | Smith et al. | |
| 4,703,004 A | 10/1987 | Hopp et al. | |
| 4,851,341 A | 7/1989 | Hopp et al. | |
| 5,011,912 A | 4/1991 | Hopp et al. | |
| 5,047,513 A | 9/1991 | Dobeli et al. | |
| 5,284,933 A | 2/1994 | Dobeli et al. | |
| 5,310,663 A | 5/1994 | Dobeli et al. | |
| 5,594,115 A | 1/1997 | Sharma | |
| 5,654,176 A | 8/1997 | Smith | |
| 5,750,374 A | 5/1998 | Dobeli et al. | |
| 5,932,102 A | 8/1999 | Wyllie et al. | |
| 6,193,966 B1 | 2/2001 | Deo et al. | |
| 6,462,254 B1 | 10/2002 | Vernachio et al. | |
| 7,094,548 B2 * | 8/2006 | Brizzard et al. | ............. 435/7.1 |
| 2002/0045193 A1 | 4/2002 | Brizzard et al. | |
| 2003/0045465 A1 * | 3/2003 | Mixson | ........................ 514/12 |
| 2003/0138839 A1 | 7/2003 | Li et al. | |

OTHER PUBLICATIONS

Rumsfeld et al. High-Throughput Assay for Inorganic Pyrophospahtases Using the Cytosolic Enzyme of *Saccharomyces cerevisiae* and Human as an Example. Protein Expression and Purification 18: 303-309, 2000.*

Zheng et al. "A new expression vector for high level protein production, one step purification and direct isotopic labeling of calmodulin-binding peptide fusion proteins" Gene, vol. 186 (1997) pp. 55-60.
Sano et al. "A streptavidin-metallothionein chimera that allows specific labeling a biological materials with many different heavy metal ions" Proc. Natl. Acad. Sci. USA, vol. 89 (Mar. 1992) pp. 1534-1538.
Maina et al. "An *Escherichia coli* vector to express and purify foreign proteins by fusion to and separation from maltose-binding protein" Gene, vol. 74 (1988) pp. 365-373.
Nygren et al. "Analysis and use of the serum albumin binding domains of streptococcal protein G" Journal of Molecular Recognition, vol. 1, No. 2 (1988) pp. 69-74.
Lauritzen et al. "BPTI and N-terminal extended analogues generated by factor Xa cleavage and cathepsin C trimming of a fusion protein expressed in *Escherichia coli*" Protein Expr. Purif., vol. 5-6 (1991) pp. 372-378 (Abstract only).
Dykes et al. "Expression of atrial natriuretic factor as a cleavable fusion protein with chloramphenicol acetyltransferase in *Escherichia coli*" Eur. J. Biochem., vol. 174 (1988) pp. 411-416.
Nilsson et al. "Fusions to Staphyloccal Protein A" Methods in Enzymology, vol. 185 (1990) pp. 144-161.
Nagai et al. "Generation of β-globin by sequence-specific proteolysis of a hybrid protein produced in *Escherichia coli*" Nature, vol. 309 (Jun. 1984) pp. 810-812.
Dan et al. "Hamster UDP-N-Acetylglucosamine:Dolichol-P N-Acetylglucosamine-1-P Transferase Has Multiple Transmembrane Spans and a Critical Cytosolic Loop" J. of Biological Chemistry, vol. 271, No. 48 (Nov. 1996) pp. 30717-30724.
Wu et al. "Hexahistidine ($His_6$)-tag dependent protein dimerization: A cautionary tale" Acta Biochemica Polonica, vol. 46, No. 3 (1999) pp. 591-599.
Vijayalakshimi "High Performance Liquid Chromatography with Immobilised Metal Adsorbents" Affinity Chromatography and Biological Recognition, Academic Press Inc., (1983) pp. 269-273.
Small et al. "High Performance Metal Chelate Chromatography" Affinity Chromatography and Biological Recognition, Academic Press, Inc. (1983) pp. 267-268.
Porath et al. "Immobilized metal ion affinity adsorption and immobilized metal ion affinity chromatography of biomaterials. Serum protein affinities for gel-immobilized iron and nickel ions" Biochemistry, vol. 22, No. 7 (1983) pp. 1621-1630.
Borjigin et al. "Insertional mutagenesis is a probe of rhodopsin's topography, stability, and activity" Journal of Biological Chemistry, vol. 269, No. 20 (1994) pp. 14715-14722.
Shoseyov et al. "Primary sequence analysis of *Clostridium cellulovorans* cellulose binding prtein A" Proc. Natl. Acad. Sci. USA, vol. 89 (1992) pp. 3483-3487.
Matsushima et al. "Purification and further characterization of enteropeptidase from porcine duodenum" J. Biochem, vol. 125 (1999) pp. 947-951.

(Continued)

*Primary Examiner*—Michele K Joike
(74) *Attorney, Agent, or Firm*—Senniger Powers LLP; Daniel Kasten

(57) ABSTRACT

This invention describes a process for separating a fusion protein or polypeptide in the form of its precursor from a mixture containing said fusion protein and impurities, which comprises contacting said fusion protein with a resin containing immobilized metal ions, said fusion protein covalently operably linked directly or indirectly to an immobilized metal ion-affinity peptide, binding said fusion protein to said resin, and selectively eluting said fusion protein from said resin.

36 Claims, No Drawings

OTHER PUBLICATIONS

Gorman et al. "Recombinant genomes which express chloramphenicol acetyltransferase in mammalian cells" Molecular and Cellular Biology, vol. 2 (1982) pp. 1044-1051.

Rodriguez-Viciana et al. "Role of Phosphoinositide 3-OH Kinase in Cell Transformation and Control of the Actin Cytoskeleton by Ras" Cell, vol. 89 (May 1997) pp. 457-467.

Smith et al. "Single-step purification of ppolypeptides expressed in *Escherichia coli* as fusions with glutathione S-transferase" Gene, vol. 67 (1988) pp. 31-40.

Moroux et al. "Synthesis of Trisacryl Sorbents for Metal Chelate Chromatography : Application to Monokine Separation" Affinity Chromatography and Biological Recognition, Academic Press, Inc. (1983) pp. 275-278.

Campbell et al. "The Alternative Carboxyl Termini of Avian Cardiac and Brain Sarcoplasmic Reticulum/Endoplasmic Reticulum $Ca^{2+}$-ATPases Are on Opposite Sides of the Membrane" Journal of Biological Chemistry, vol. 267, No. 13 (May 1992) pp. 9321-9325.

Chang "Thrombin Specificity: Requirement for apolar amino acids adjacent to the thrombin cleavage site of polypeptide substrate" Eur. J. Biochem., vol. 151 (1985) pp. 217-224.

Cubitt et al. "Understanding, improving and using green fluorescent proteins" TIBS, vol. 20 (1995) pp. 448-455.

Sato et al. "Universal Template Plasmid for Introduction of the Tripple-HA Epitope Sequence into Cloned Genes" Biotechniques, vol. 23, No. 2 (1997) pp. 254-256.

Germino et al. "Use of gene fusions and protein-protein interaction in the isolation of a biologically active regulatory protein: The replication initiator protein of plasmid R6K" Proc. Natl. Acad. Sci. USA, vol. 80 (1983) pp. 6848-6852.

Brizzard, B.L., et al., "Immunoaffinity Purification of FLAG Epitope-Tagged Bacterial Alkaline Phosphatase Using a Novel Monoclonal Antibody and Peptide Elution," BioTechniques, 1994, vol. 16(4), pp. 730-734.

Galfre, G., et al., "Chapter 1. Preparation of Monoclonal Antibodies," Methods in Enzymology, 1981, vol. 73, pp. 3-46, Academic Press, New York, New York.

Koren, E., et al., "Characterization of a Monoclonal Antibody that Binds Equally to All Apolipoprotein and Lipoprotein Forms of Human Plasma Apolipoprotein B. I. Specificity and Binding Studies," Biochim Biophys Acta, 1986, vol. 876, pp. 91-100.

Kunz, D., et al., "The Human Leukocyte Platelet-Activating Factor Receptor," J Biol Chem, 1992, vol. 267(13), pp. 9101-9106.

Lauritzen, C., et al., "BPTI and N-Terminal Extended Analogues Generated by Factor Xa Cleavage and Cathepsin C Trimming of a Fusion Protein Expressed in *Escherichia coli*," Protein Expression and Purification, 1991, vol. 2, pp. 372-378.

Rodriguez-Viciana, P., et al., "Role of Phosphoinositide 3-OH Kinase in Cell Transformation and Control of the Actin Cytoskeleton by Ras," Cell, 1997, vol. 89, pp. 457-467.

Wu, J., et al., "Hexahistidine (His6)-tag Dependent Protein Dimerization: A Cautionary Tale," Acta Biochimica Polonica, 1999, vol. 46(3), pp. 591-599.

"Chapter 7. Immunoprecipitation," Antibodies: A Laboratory Manual, 2nd Edition, 1988, pp. 223-255, Cold Spring Harbor Press, New York.

Non-final Office action dated Jan. 11, 2008, issued in U.S. Appl. No. 11/128,486, 7 pages.

Non-final Office action dated Jan. 28, 2009, issued in U.S. Appl. No. 11/128,486, 11 pages.

* cited by examiner

SEQUENCE LISTING

```
<160> NUMBER OF SEQ ID NOS: 46

<210> SEQ ID NO 1
<211> LENGTH: 211
<212> TYPE: PRT
<213> ORGANISM: Shistosoma japonicum

<400> SEQUENCE: 1

Met Ala Cys Gly His Val Lys Leu Ile Tyr Phe Asn Gly Arg Gly Arg
1               5                   10                  15

Ala Glu Pro Ile Arg Met Ile Leu Val Ala Ala Gly Val Glu Phe Glu
            20                  25                  30

Asp Glu Arg Ile Glu Phe Gln Asp Trp Pro Lys Ile Lys Pro Thr Ile
        35                  40                  45

Pro Gly Gly Arg Leu Pro Ile Val Lys Ile Thr Asp Lys Arg Gly Asp
    50                  55                  60

Val Lys Thr Met Ser Glu Ser Leu Ala Ile Ala Arg Phe Ile Ala Arg
65                  70                  75                  80

Lys His Asn Met Met Gly Asp Thr Asp Glu Tyr Tyr Ile Ile Glu
                85                  90                  95

Lys Met Ile Gly Gln Val Glu Asp Val Glu Ser Asp Tyr His Lys Thr
                100                 105                 110
```

```
Leu Ile Lys Pro Pro Glu Glu Lys Glu Lys Ile Ser Lys Glu Ile Leu
        115                 120                 125

Asn Gly Lys Val Pro Ile Leu Leu Gln Ala Ile Cys Glu Thr Leu Lys
    130                 135                 140

Glu Ser Thr Gly Asn Leu Thr Val Gly Asp Lys Val Thr Leu Ala Asp
145                 150                 155                 160

Val Val Leu Ile Ala Ser Ile Asp His Ile Thr Asp Leu Asp Lys Glu
                165                 170                 175

Phe Leu Thr Gly Lys Tyr Pro Glu Ile His Lys His Arg Lys His Leu
            180                 185                 190

Leu Ala Thr Ser Pro Lys Leu Ala Lys Tyr Leu Ser Glu Arg His Ala
        195                 200                 205

Thr Ala Phe
    210

<210> SEQ ID NO 2
<211> LENGTH: 163
<212> TYPE: PRT
<213> ORGANISM: Clostridium cellulovorans

<400> SEQUENCE: 2

Ala Ala Thr Ser Ser Met Ser Val Glu Phe Tyr Asn Ser Asn Lys Ser
1               5                   10                  15

Ala Gln Thr Asn Ser Ile Thr Pro Ile Ile Lys Ile Thr Asn Thr Ser
            20                  25                  30

Asp Ser Asp Leu Asn Leu Asn Asp Val Lys Val Arg Tyr Thr Tyr Tyr
        35                  40                  45

Thr Ser Asp Gly Thr Gln Gly Gln Thr Phe Trp Cys Asp His Ala Gly
    50                  55                  60

Ala Leu Leu Gly Asn Ser Tyr Val Asp Asn Thr Ser Lys Val Thr Ala
65              70                  75                  80

Asn Phe Val Lys Glu Thr Ala Ser Pro Thr Ser Thr Tyr Asp Thr Tyr
                85                  90                  95

Val Glu Phe Gly Phe Ala Ser Gly Ala Ala Thr Leu Lys Lys Gly Gln
            100                 105                 110

Phe Ile Thr Ile Gln Gly Arg Ile Thr Lys Ser Asp Trp Ser Asn Tyr
        115                 120                 125

Thr Gln Thr Asn Asp Tyr Ser Phe Asp Ala Ser Ser Ser Thr Pro Val
    130                 135                 140

Val Asn Pro Lys Val Thr Gly Tyr Ile Gly Gly Ala Lys Val Leu Gly
145                 150                 155                 160

Thr Ala Pro

<210> SEQ ID NO 3
<211> LENGTH: 396
<212> TYPE: PRT
<213> ORGANISM: Escherichia coli

<400> SEQUENCE: 3

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
```

-continued

```
                    50                  55                  60
His Pro Asp Lys Leu Glu Glu Lys Phe Pro Gln Val Ala Ala Thr Gly
 65                  70                  75                  80

Asp Gly Pro Asp Ile Ile Phe Trp Ala His Asp Arg Phe Gly Gly Tyr
                 85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255

Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Arg Ile Thr Lys
385                 390                 395

<210> SEQ ID NO 4
<211> LENGTH: 524
<212> TYPE: PRT
<213> ORGANISM: Staphylococcus aureus

<400> SEQUENCE: 4

Met Lys Lys Lys Asn Ile Tyr Ser Ile Arg Lys Leu Gly Val Gly Ile
  1               5                  10                  15

Ala Ser Val Thr Leu Gly Thr Leu Leu Ile Ser Gly Gly Val Thr Pro
             20                  25                  30
```

-continued

```
Ala Ala Asn Ala Ala Gln His Asp Glu Ala Gln Gln Asn Ala Phe Tyr
        35                  40                  45
Gln Val Leu Asn Met Pro Asn Leu Asn Ala Asp Gln Arg Asn Gly Phe
    50                  55                  60
Ile Gln Ser Leu Lys Asp Asp Pro Ser Gln Ser Ala Asn Val Leu Gly
65                  70                  75                  80
Glu Ala Gln Lys Leu Asn Asp Ser Gln Ala Pro Lys Ala Asp Ala Gln
                85                  90                  95
Gln Asn Asn Phe Asn Lys Asp Gln Gln Ser Ala Phe Tyr Glu Ile Leu
            100                 105                 110
Asn Met Pro Asn Leu Asn Glu Ala Gln Arg Asn Gly Phe Ile Gln Ser
        115                 120                 125
Leu Lys Asp Asp Pro Ser Gln Ser Thr Asn Val Leu Gly Glu Ala Lys
    130                 135                 140
Lys Leu Asn Glu Ser Gln Ala Pro Lys Ala Asp Asn Asn Phe Asn Lys
145                 150                 155                 160
Glu Gln Gln Asn Ala Phe Tyr Glu Ile Leu Asn Met Pro Asn Leu Asn
                165                 170                 175
Glu Glu Gln Arg Asn Gly Phe Ile Gln Ser Leu Lys Asp Asp Pro Ser
            180                 185                 190
Gln Ser Ala Asn Leu Leu Ser Glu Ala Lys Lys Leu Asn Glu Ser Gln
        195                 200                 205
Ala Pro Lys Ala Asp Asn Lys Phe Asn Lys Glu Gln Gln Asn Ala Phe
    210                 215                 220
Tyr Glu Ile Leu His Leu Pro Asn Leu Asn Glu Glu Gln Arg Asn Gly
225                 230                 235                 240
Phe Ile Gln Ser Leu Lys Asp Asp Pro Ser Gln Ser Ala Asn Leu Leu
                245                 250                 255
Ala Glu Ala Lys Lys Leu Asn Asp Ala Gln Ala Pro Lys Ala Asp Asn
            260                 265                 270
Lys Phe Asn Lys Glu Gln Gln Asn Ala Phe Tyr Glu Ile Leu His Leu
        275                 280                 285
Pro Asn Leu Thr Glu Glu Gln Arg Asn Gly Phe Ile Gln Ser Leu Lys
    290                 295                 300
Asp Asp Pro Ser Val Ser Lys Glu Ile Leu Ala Glu Ala Lys Lys Leu
305                 310                 315                 320
Asn Asp Ala Gln Ala Pro Lys Glu Glu Asp Asn Asn Lys Pro Gly Lys
                325                 330                 335
Glu Asp Asn Asn Lys Pro Gly Lys Glu Asp Asn Asn Lys Pro Gly Lys
            340                 345                 350
Glu Asp Asn Asn Lys Pro Gly Lys Glu Asp Asn Asn Lys Pro Gly Lys
        355                 360                 365
Glu Asp Asn Asn Lys Pro Gly Lys Glu Asp Gly Asn Lys Pro Gly Lys
    370                 375                 380
Glu Asp Asn Lys Lys Pro Gly Lys Glu Asp Gly Asn Lys Pro Gly Lys
385                 390                 395                 400
Glu Asp Asn Lys Lys Pro Gly Lys Glu Asp Gly Asn Lys Pro Gly Lys
                405                 410                 415
Glu Asp Gly Asn Lys Pro Gly Lys Glu Asp Gly Asn Gly Val His Val
            420                 425                 430
Val Lys Pro Gly Asp Thr Val Asn Asp Ile Ala Lys Ala Asn Gly Thr
        435                 440                 445
Thr Ala Asp Lys Ile Ala Ala Asp Asn Lys Leu Ala Asp Lys Asn Met
```

```
          450                 455                 460
Ile Lys Pro Gly Gln Glu Leu Val Val Asp Lys Lys Gln Pro Ala Asn
465                 470                 475                 480

His Ala Asp Ala Asn Lys Ala Gln Ala Leu Pro Glu Thr Gly Glu Glu
                485                 490                 495

Asn Pro Phe Ile Gly Thr Thr Val Phe Gly Gly Leu Ser Leu Ala Leu
            500                 505                 510

Gly Ala Ala Leu Leu Ala Gly Arg Arg Arg Glu Leu
            515                 520

<210> SEQ ID NO 5
<211> LENGTH: 448
<212> TYPE: PRT
<213> ORGANISM: Streptococcus

<400> SEQUENCE: 5

Met Glu Lys Glu Lys Lys Val Lys Tyr Phe Leu Arg Lys Ser Ala Phe
1               5                   10                  15

Gly Leu Ala Ser Val Ser Ala Ala Phe Leu Val Gly Ser Thr Val Phe
            20                  25                  30

Ala Val Asp Ser Pro Ile Glu Asp Thr Pro Ile Ile Arg Asn Gly Gly
        35                  40                  45

Glu Leu Thr Asn Leu Leu Gly Asn Ser Glu Thr Thr Leu Ala Leu Arg
    50                  55                  60

Asn Glu Glu Ser Ala Thr Ala Asp Leu Thr Ala Ala Val Ala Asp
65                  70                  75                  80

Thr Val Ala Ala Ala Ala Glu Asn Ala Gly Ala Ala Ala Trp Glu
                85                  90                  95

Ala Ala Ala Ala Asp Ala Leu Ala Lys Ala Lys Ala Asp Ala Leu
            100                 105                 110

Lys Glu Phe Asn Lys Tyr Gly Val Ser Asp Tyr Lys Asn Leu Ile
            115                 120                 125

Asn Asn Ala Lys Thr Val Glu Gly Ile Lys Asp Leu Gln Ala Gln Val
130                 135                 140

Val Glu Ser Ala Lys Lys Ala Arg Ile Ser Glu Ala Thr Asp Gly Leu
145                 150                 155                 160

Ser Asp Phe Leu Lys Ser Gln Thr Pro Ala Glu Asp Thr Val Lys Ser
                165                 170                 175

Ile Glu Leu Ala Glu Ala Lys Val Leu Ala Asn Arg Glu Leu Asp Lys
            180                 185                 190

Tyr Gly Val Ser Asp Tyr His Lys Asn Leu Ile Asn Asn Ala Lys Thr
            195                 200                 205

Val Glu Gly Val Lys Glu Leu Ile Asp Glu Ile Leu Ala Ala Leu Pro
        210                 215                 220

Lys Thr Asp Thr Tyr Lys Leu Ile Leu Asn Gly Lys Thr Leu Lys Gly
225                 230                 235                 240

Glu Thr Thr Thr Glu Ala Val Asp Ala Ala Thr Ala Glu Lys Val Phe
                245                 250                 255

Lys Gln Tyr Ala Asn Asp Asn Gly Val Asp Gly Glu Trp Thr Tyr Asp
            260                 265                 270

Asp Ala Thr Lys Thr Phe Thr Val Thr Glu Lys Pro Glu Val Ile Asp
        275                 280                 285

Ala Ser Glu Leu Thr Pro Ala Val Thr Thr Tyr Lys Leu Val Ile Asn
    290                 295                 300
```

```
Gly Lys Thr Leu Lys Gly Glu Thr Thr Thr Lys Ala Val Asp Ala Glu
305                 310                 315                 320

Thr Ala Glu Lys Ala Phe Lys Gln Tyr Ala Asn Asp Asn Gly Val Asp
            325                 330                 335

Gly Val Trp Thr Tyr Asp Asp Ala Thr Lys Thr Phe Thr Val Thr Glu
                340                 345                 350

Met Val Thr Glu Val Pro Gly Asp Ala Pro Thr Glu Pro Glu Lys Pro
        355                 360                 365

Glu Ala Ser Ile Pro Leu Val Pro Leu Thr Pro Ala Thr Pro Ile Ala
    370                 375                 380

Lys Asp Asp Ala Lys Lys Asp Asp Thr Lys Lys Glu Asp Ala Lys Lys
385                 390                 395                 400

Pro Glu Ala Lys Lys Asp Asp Ala Lys Lys Ala Glu Thr Leu Pro Thr
                405                 410                 415

Thr Gly Glu Gly Ser Asn Pro Phe Phe Thr Ala Ala Leu Ala Val
        420                 425                 430

Met Ala Gly Ala Gly Ala Leu Ala Val Ala Ser Lys Arg Lys Glu Asp
        435                 440                 445
```

<210> SEQ ID NO 6
<211> LENGTH: 192
<212> TYPE: PRT
<213> ORGANISM: Homo sapiens

<400> SEQUENCE: 6

```
Met Ala Pro Ser Leu Ser Ala Met Thr Pro Trp Thr Pro Gly Pro Ser
1               5                   10                  15

Trp Ser Ser Val Tyr Met Thr Cys Val Trp Ser Val Gly Ser Gly Ser
                20                  25                  30

Ala Cys Ala Val Ala Ser Ala Pro Met Pro Arg Pro Val Trp Ser Leu
            35                  40                  45

Ala Ser Arg Leu Gly Thr Gly Asp His Gln Pro Thr Ala Pro Cys Pro
        50                  55                  60

Ala Leu Pro Thr Ala Ala Met Ser Ser Ala Ala Leu Leu Ala Arg Pro
65                  70                  75                  80

Pro Ala Thr Gly Leu Arg Arg Arg Pro Thr Ala Pro Gly Ala Pro Ala
                85                  90                  95

Trp Arg Ala Ala Cys Ala Ser Gln Ala Ser Trp Pro Ala Ala Ala Pro
            100                 105                 110

Ala Cys Arg Pro Arg Arg Val Ala Pro Ser Arg Val Ser Ser Ser
            115                 120                 125

Leu Arg Ala Arg Lys Cys Gly Arg Thr Ser Cys Ala Lys Gly Ala Ala
        130                 135                 140

Pro Ala Thr Ala Pro Pro Ile Arg Ser Pro Ala Ala Thr Ser Arg Ala
145                 150                 155                 160

Ala Arg Arg Val Ser Ala Ala Ser Arg Thr Ala Ser Trp Ala Ala
                165                 170                 175

Thr Pro Ile Ala Ser Gly Pro Ala Arg Gly Pro Gly Thr His Thr Met
            180                 185                 190
```

<210> SEQ ID NO 7
<211> LENGTH: 216
<212> TYPE: PRT
<213> ORGANISM: Escherichia coli

<400> SEQUENCE: 7

```
Met Asn Phe Asn Lys Ile Asp Leu Asp Asn Trp Lys Arg Lys Glu Ile
1               5                   10                  15

Phe Asn His Tyr Leu Asn Gln Gln Thr Thr Phe Ser Ile Thr Thr Glu
            20                  25                  30

Ile Asp Ile Ser Val Leu Tyr Arg Asn Ile Lys Gln Glu Gly Tyr Lys
        35                  40                  45

Phe Tyr Pro Ala Phe Ile Phe Leu Val Thr Arg Val Ile Asn Ser Asn
    50                  55                  60

Thr Ala Phe Arg Thr Gly Tyr Asn Ser Asp Gly Glu Leu Gly Tyr Trp
65                  70                  75                  80

Asp Lys Leu Glu Pro Leu Tyr Thr Ile Phe Asp Gly Val Ser Lys Thr
                85                  90                  95

Phe Ser Gly Ile Trp Thr Pro Val Lys Asn Asp Phe Lys Glu Phe Tyr
            100                 105                 110

Asp Leu Tyr Leu Ser Asp Val Glu Lys Tyr Asn Gly Ser Gly Lys Leu
        115                 120                 125

Phe Pro Lys Thr Pro Ile Pro Glu Asn Ala Phe Ser Leu Ser Ile Ile
    130                 135                 140

Pro Trp Thr Ser Phe Thr Gly Phe Asn Leu Asn Ile Asn Asn Asn Ser
145                 150                 155                 160

Asn Tyr Leu Leu Pro Ile Ile Thr Ala Gly Lys Phe Ile Asn Lys Gly
                165                 170                 175

Asn Ser Ile Tyr Leu Pro Leu Ser Leu Gln Val His His Ser Val Cys
            180                 185                 190

Asp Gly Tyr His Ala Gly Leu Phe Met Asn Ser Ile Gln Glu Leu Ser
        195                 200                 205

Asp Arg Pro Asn Asp Trp Leu Leu
    210                 215

<210> SEQ ID NO 8
<211> LENGTH: 160
<212> TYPE: PRT
<213> ORGANISM: Streptomyces avidinii

<400> SEQUENCE: 8

Met Asp Pro Ser Lys Asp Ser Lys Ala Gln Val Ser Ala Ala Glu Ala
1               5                   10                  15

Gly Ile Thr Gly Thr Trp Tyr Asn Gln Leu Gly Ser Thr Phe Ile Val
            20                  25                  30

Thr Ala Gly Ala Asp Gly Ala Leu Thr Gly Thr Tyr Glu Ser Ala Val
        35                  40                  45

Gly Asn Ala Glu Ser Arg Tyr Val Leu Thr Gly Arg Tyr Asp Ser Ala
    50                  55                  60

Pro Ala Thr Asp Gly Ser Gly Thr Ala Leu Gly Trp Thr Val Ala Trp
65                  70                  75                  80

Lys Asn Asn Tyr Arg Asn Ala His Ser Ala Thr Thr Trp Ser Gly Gln
                85                  90                  95

Tyr Val Gly Gly Ala Glu Ala Arg Ile Asn Thr Gln Trp Leu Leu Thr
            100                 105                 110

Ser Gly Thr Thr Glu Ala Asn Ala Trp Lys Ser Thr Leu Val Gly His
        115                 120                 125

Asp Thr Phe Thr Lys Val Lys Pro Ser Ala Ala Ser Ile Asp Ala Ala
    130                 135                 140

Lys Lys Ala Gly Val Asn Asn Gly Asn Pro Leu Asp Ala Val Gln Gln
145                 150                 155                 160
```

<210> SEQ ID NO 9
<211> LENGTH: 1024
<212> TYPE: PRT
<213> ORGANISM: Escherichia coli

<400> SEQUENCE: 9

```
Met Thr Met Ile Thr Asp Ser Leu Ala Val Val Leu Gln Arg Arg Asp
1               5                   10                  15

Trp Glu Asn Pro Gly Val Thr Gln Leu Asn Arg Leu Ala Ala His Pro
            20                  25                  30

Pro Phe Ala Ser Trp Arg Asn Ser Glu Glu Ala Arg Thr Asp Arg Pro
        35                  40                  45

Ser Gln Gln Leu Arg Ser Leu Asn Gly Glu Trp Arg Phe Ala Trp Phe
    50                  55                  60

Pro Ala Pro Glu Ala Val Pro Glu Ser Trp Leu Glu Cys Asp Leu Pro
65                  70                  75                  80

Glu Ala Asp Thr Val Val Pro Ser Asn Trp Gln Met His Gly Tyr
                85                  90                  95

Asp Ala Pro Ile Tyr Thr Asn Val Thr Tyr Pro Ile Thr Val Asn Pro
            100                 105                 110

Pro Phe Val Pro Thr Glu Asn Pro Thr Gly Cys Tyr Ser Leu Thr Phe
        115                 120                 125

Asn Val Asp Glu Ser Trp Leu Gln Glu Gly Gln Thr Arg Ile Ile Phe
    130                 135                 140

Asp Gly Val Asn Ser Ala Phe His Leu Trp Cys Asn Gly Arg Trp Val
145                 150                 155                 160

Gly Tyr Gly Gln Asp Ser Arg Leu Pro Ser Glu Phe Asp Leu Ser Ala
                165                 170                 175

Phe Leu Arg Ala Gly Glu Asn Arg Leu Ala Val Met Val Leu Arg Trp
            180                 185                 190

Ser Asp Gly Ser Tyr Leu Glu Asp Gln Asp Met Trp Arg Met Ser Gly
        195                 200                 205

Ile Phe Arg Asp Val Ser Leu Leu His Lys Pro Thr Thr Gln Ile Ser
    210                 215                 220

Asp Phe His Val Ala Thr Arg Phe Asn Asp Asp Phe Ser Arg Ala Val
225                 230                 235                 240

Leu Glu Ala Glu Val Gln Met Cys Gly Glu Leu Arg Asp Tyr Leu Arg
                245                 250                 255

Val Thr Val Ser Leu Trp Gln Gly Glu Thr Gln Val Ala Ser Gly Thr
            260                 265                 270

Ala Pro Phe Gly Gly Glu Ile Ile Asp Glu Arg Gly Gly Tyr Ala Asp
        275                 280                 285

Arg Val Thr Leu Arg Leu Asn Val Glu Asn Pro Lys Leu Trp Ser Ala
    290                 295                 300

Glu Ile Pro Asn Leu Tyr Arg Ala Val Val Glu Leu His Thr Ala Asp
305                 310                 315                 320

Gly Thr Leu Ile Glu Ala Glu Ala Cys Asp Val Gly Phe Arg Glu Val
                325                 330                 335

Arg Ile Glu Asn Gly Leu Leu Leu Leu Asn Gly Lys Pro Leu Leu Ile
            340                 345                 350

Arg Gly Val Asn Arg His Glu His His Pro Leu His Gly Gln Val Met
        355                 360                 365

Asp Glu Gln Thr Met Val Gln Asp Ile Leu Leu Met Lys Gln Asn Asn
```

-continued

```
              370                 375                 380
Phe Asn Ala Val Arg Cys Ser His Tyr Pro Asn His Pro Leu Trp Tyr
385                 390                 395                 400

Thr Leu Cys Asp Arg Tyr Gly Leu Tyr Val Val Asp Glu Ala Asn Ile
                405                 410                 415

Glu Thr His Gly Met Val Pro Met Asn Arg Leu Thr Asp Asp Pro Arg
                420                 425                 430

Trp Leu Pro Ala Met Ser Glu Arg Val Thr Arg Met Val Gln Arg Asp
                435                 440                 445

Arg Asn His Pro Ser Val Ile Ile Trp Ser Leu Gly Asn Glu Ser Gly
450                 455                 460

His Gly Ala Asn His Asp Ala Leu Tyr Arg Trp Ile Lys Ser Val Asp
465                 470                 475                 480

Pro Ser Arg Pro Val Gln Tyr Glu Gly Gly Ala Asp Thr Thr Ala
                485                 490                 495

Thr Asp Ile Ile Cys Pro Met Tyr Ala Arg Val Asp Glu Asp Gln Pro
                500                 505                 510

Phe Pro Ala Val Pro Lys Trp Ser Ile Lys Lys Trp Leu Ser Leu Pro
                515                 520                 525

Gly Glu Thr Arg Pro Leu Ile Leu Cys Glu Tyr Ala His Ala Met Gly
                530                 535                 540

Asn Ser Leu Gly Gly Phe Ala Lys Tyr Trp Gln Ala Phe Arg Gln Tyr
545                 550                 555                 560

Pro Arg Leu Gln Gly Gly Phe Val Trp Asp Trp Val Asp Gln Ser Leu
                565                 570                 575

Ile Lys Tyr Asp Glu Asn Gly Asn Pro Trp Ser Ala Tyr Gly Gly Asp
                580                 585                 590

Phe Gly Asp Thr Pro Asn Asp Arg Gln Phe Cys Met Asn Gly Leu Val
                595                 600                 605

Phe Ala Asp Arg Thr Pro His Pro Ala Leu Thr Glu Ala Lys His Gln
                610                 615                 620

Gln Gln Phe Phe Gln Phe Arg Leu Ser Gly Gln Thr Ile Glu Val Thr
625                 630                 635                 640

Ser Glu Tyr Leu Phe Arg His Ser Asp Asn Glu Leu Leu His Trp Met
                645                 650                 655

Val Ala Leu Asp Gly Lys Pro Leu Ala Ser Gly Glu Val Pro Leu Asp
                660                 665                 670

Val Ala Pro Gln Gly Lys Gln Leu Ile Glu Leu Pro Glu Leu Pro Gln
                675                 680                 685

Pro Glu Ser Ala Gly Gln Leu Trp Leu Thr Val Arg Val Val Gln Pro
                690                 695                 700

Asn Ala Thr Ala Trp Ser Glu Ala Gly His Ile Ser Ala Trp Gln Gln
705                 710                 715                 720

Trp Arg Leu Ala Glu Asn Leu Ser Val Thr Leu Pro Ala Ala Ser His
                725                 730                 735

Ala Ile Pro His Leu Thr Thr Ser Glu Met Asp Phe Cys Ile Glu Leu
                740                 745                 750

Gly Asn Lys Arg Trp Gln Phe Asn Arg Gln Ser Gly Phe Leu Ser Gln
                755                 760                 765

Met Trp Ile Gly Asp Lys Lys Gln Leu Leu Thr Pro Leu Arg Asp Gln
                770                 775                 780

Phe Thr Arg Ala Pro Leu Asp Asn Asp Ile Gly Val Ser Glu Ala Thr
785                 790                 795                 800
```

-continued

Arg Ile Asp Pro Asn Ala Trp Val Glu Arg Trp Lys Ala Ala Gly His
                805                 810                 815

Tyr Gln Ala Glu Ala Leu Leu Gln Cys Thr Ala Asp Thr Leu Ala
            820                 825                 830

Asp Ala Val Leu Ile Thr Thr Ala His Ala Trp Gln His Gln Gly Lys
            835                 840                 845

Thr Leu Phe Ile Ser Arg Lys Thr Tyr Arg Ile Asp Gly Ser Gly Gln
        850                 855                 860

Met Ala Ile Thr Val Asp Val Glu Val Ala Ser Asp Thr Pro His Pro
865                 870                 875                 880

Ala Arg Ile Gly Leu Asn Cys Gln Leu Ala Gln Val Ala Glu Arg Val
                885                 890                 895

Asn Trp Leu Gly Leu Gly Pro Gln Glu Asn Tyr Pro Asp Arg Leu Thr
            900                 905                 910

Ala Ala Cys Phe Asp Arg Trp Asp Leu Pro Leu Ser Asp Met Tyr Thr
        915                 920                 925

Pro Tyr Val Phe Pro Ser Glu Asn Gly Leu Arg Cys Gly Thr Arg Glu
    930                 935                 940

Leu Asn Tyr Gly Pro His Gln Trp Arg Gly Asp Phe Gln Phe Asn Ile
945                 950                 955                 960

Ser Arg Tyr Ser Gln Gln Gln Leu Met Glu Thr Ser His Arg His Leu
                965                 970                 975

Leu His Ala Glu Glu Gly Thr Trp Leu Asn Ile Asp Gly Phe His Met
            980                 985                 990

Gly Ile Gly Gly Asp Asp Ser Trp Ser Pro Ser Val Ser Ala Glu Phe
        995                 1000                1005

Gln Leu Ser Ala Gly Arg Tyr His Tyr Gln Leu Val Trp Cys Gln
    1010                1015                1020

Lys

<210> SEQ ID NO 10
<211> LENGTH: 238
<212> TYPE: PRT
<213> ORGANISM: Aequorea victoria

<400> SEQUENCE: 10

Met Ser Lys Gly Glu Glu Leu Phe Thr Gly Val Val Pro Ile Leu Val
1               5                   10                  15

Glu Leu Asp Gly Asp Val Asn Gly Gln Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Tyr Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Met Glu Tyr Asn
    130                 135                 140

```
Tyr Asn Ser His Asn Val Tyr Ile Met Ala Asp Lys Pro Lys Asn Gly
145                 150                 155                 160

Ile Lys Val Asn Phe Lys Ile Arg His Asn Ile Lys Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Ile Leu Leu Glu Phe Val
    210                 215                 220

Thr Ala Ala Gly Ile Thr His Gly Met Asp Glu Leu Tyr Lys
225                 230                 235

<210> SEQ ID NO 11
<211> LENGTH: 109
<212> TYPE: PRT
<213> ORGANISM: Escherichia coli

<400> SEQUENCE: 11

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105

<210> SEQ ID NO 12
<211> LENGTH: 13
<212> TYPE: PRT
<213> ORGANISM: Oryctolagus cuniculus

<400> SEQUENCE: 12

Ile Ala Val Ser Ala Ala Asn Arg Phe Lys Lys Ile Ser
1               5                   10

<210> SEQ ID NO 13
<211> LENGTH: 10
<212> TYPE: PRT
<213> ORGANISM: artificial sequence
<220> FEATURE:
<223> OTHER INFORMATION: synthetic c-myc epitope

<400> SEQUENCE: 13

Glu Gln Lys Leu Ile Ser Glu Glu Asp Leu
1               5                   10

<210> SEQ ID NO 14
<211> LENGTH: 7
<212> TYPE: PRT
<213> ORGANISM: artificial sequence
<220> FEATURE:
<223> OTHER INFORMATION: synthetic HA epitope
```

-continued

```
<400> SEQUENCE: 14

Tyr Pro Tyr Asp Val Tyr Ala
1               5

<210> SEQ ID NO 15
<211> LENGTH: 8
<212> TYPE: PRT
<213> ORGANISM: artificial sequence
<220> FEATURE:
<223> OTHER INFORMATION: synthetic FLAG sequence

<400> SEQUENCE: 15

Asp Tyr Lys Asp Asp Asp Asp Lys
1               5

<210> SEQ ID NO 16
<211> LENGTH: 8
<212> TYPE: PRT
<213> ORGANISM: artificial sequence
<220> FEATURE:
<223> OTHER INFORMATION: synthetic Invitorgen sequence

<400> SEQUENCE: 16

Asp Leu Tyr Asp Asp Asp Asp Lys
1               5

<210> SEQ ID NO 17
<211> LENGTH: 23
<212> TYPE: PRT
<213> ORGANISM: artificial sequence
<220> FEATURE:
<223> OTHER INFORMATION: synthetic 3X FLAG sequence

<400> SEQUENCE: 17

Met Asp Tyr Lys Asp His Asp Gly Asp Tyr Lys Asp His Asp Ile Asp
1               5                   10                  15

Tyr Lys Asp Asp Asp Asp Lys
            20

<210> SEQ ID NO 18
<211> LENGTH: 30
<212> TYPE: DNA
<213> ORGANISM: artificial sequence
<220> FEATURE:
<223> OTHER INFORMATION: chemically synthesized oligonucleotide
<220> FEATURE:
<221> NAME/KEY: misc_feature
<222> LOCATION: (10)..(10)
<223> OTHER INFORMATION: N= A, G, T or C
<220> FEATURE:
<221> NAME/KEY: misc_feature
<222> LOCATION: (9)..(9)
<223> OTHER INFORMATION: D=A, G, or T
<220> FEATURE:
<221> NAME/KEY: misc_feature
<222> LOCATION: (11)..(11)
<223> OTHER INFORMATION: D=A, G, or T
<220> FEATURE:
<221> NAME/KEY: misc_feature
<222> LOCATION: (15)..(15)
<223> OTHER INFORMATION: D=A, G, or T
<220> FEATURE:
<221> NAME/KEY: misc_feature
<222> LOCATION: (17)..(17)
<223> OTHER INFORMATION: D=A, G, or T
<220> FEATURE:
<221> NAME/KEY: misc_feature
<222> LOCATION: (21)..(21)
<223> OTHER INFORMATION: D=A, G, or T
```

```
<220> FEATURE:
<221> NAME/KEY: misc_feature
<222> LOCATION: (23)..(23)
<223> OTHER INFORMATION: D=A, G, or T
<220> FEATURE:
<221> NAME/KEY: misc_feature
<222> LOCATION: (16)..(16)
<223> OTHER INFORMATION: N= A, G, T or C
<220> FEATURE:
<221> NAME/KEY: misc_feature
<222> LOCATION: (22)..(22)
<223> OTHER INFORMATION: N= A, G, T or C

<400> SEQUENCE: 18
gatcccatdn dcatdndcat dndcattaac                                    30

<210> SEQ ID NO 19
<211> LENGTH: 30
<212> TYPE: DNA
<213> ORGANISM: artificial sequence
<220> FEATURE:
<223> OTHER INFORMATION: chemically synthesized oligonucleotide
<220> FEATURE:
<221> NAME/KEY: misc_feature
<222> LOCATION: (13)..(13)
<223> OTHER INFORMATION: N= A, G, T, or C
<220> FEATURE:
<221> NAME/KEY: misc_feature
<222> LOCATION: (14)..(14)
<223> OTHER INFORMATION: H= A, C, or T
<220> FEATURE:
<221> NAME/KEY: misc_feature
<222> LOCATION: (18)..(18)
<223> OTHER INFORMATION: H= A, C, or T
<220> FEATURE:
<221> NAME/KEY: misc_feature
<222> LOCATION: (20)..(20)
<223> OTHER INFORMATION: H= A, C, or T
<220> FEATURE:
<221> NAME/KEY: misc_feature
<222> LOCATION: (24)..(24)
<223> OTHER INFORMATION: H= A, C, or T
<220> FEATURE:
<221> NAME/KEY: misc_feature
<222> LOCATION: (26)..(26)
<223> OTHER INFORMATION: H= A, C, or T
<220> FEATURE:
<221> NAME/KEY: misc_feature
<222> LOCATION: (19)..(19)
<223> OTHER INFORMATION: N= A, G, T, or C
<220> FEATURE:
<221> NAME/KEY: misc_feature
<222> LOCATION: (25)..(25)
<223> OTHER INFORMATION: N= A, G, T, or C
<220> FEATURE:
<221> NAME/KEY: misc_feature
<222> LOCATION: (12)..(12)
<223> OTHER INFORMATION: H= A, C, or T

<400> SEQUENCE: 19
aattgttaat ghnhatghnh atghnhatgg                                    30

<210> SEQ ID NO 20
<211> LENGTH: 26
<212> TYPE: DNA
<213> ORGANISM: artificial sequence
<220> FEATURE:
<223> OTHER INFORMATION: chemically synthesized oligonucleotide

<400> SEQUENCE: 20
tatgcataat catcgacatg aacata                                        26

<210> SEQ ID NO 21
```

```
<211> LENGTH: 28
<212> TYPE: DNA
<213> ORGANISM: artificial sequence
<220> FEATURE:
<223> OTHER INFORMATION: chemically synthesized oligonucleotide

<400> SEQUENCE: 21
agcttatgtt tatgtcgatg attatgca                                            28

<210> SEQ ID NO 22
<211> LENGTH: 26
<212> TYPE: DNA
<213> ORGANISM: artificial sequence
<220> FEATURE:
<223> OTHER INFORMATION: chemically synthesized oligonucleotide

<400> SEQUENCE: 22
tatgcataaa catagacatg ggcata                                              26

<210> SEQ ID NO 23
<211> LENGTH: 29
<212> TYPE: DNA
<213> ORGANISM: artificial sequence
<220> FEATURE:
<223> OTHER INFORMATION: chemically synthesized oligonucleotide

<400> SEQUENCE: 23
agcttgatgc ccatgtctat gtttatgca                                           29

<210> SEQ ID NO 24
<211> LENGTH: 7
<212> TYPE: PRT
<213> ORGANISM: Artificial Sequence
<220> FEATURE:
<223> OTHER INFORMATION: metal-ion affinity peptide
<220> FEATURE:
<221> NAME/KEY: MISC_FEATURE
<222> LOCATION: (2)..(2)
<223> OTHER INFORMATION: Xaa = any amino acid selected from the
      following group: Ala or Arg or Asn or Asp or Gln or Glu or Ile
      or Lys or Phe or Pro of Ser or Thr or Trp or Val.
<220> FEATURE:
<221> NAME/KEY: MISC_FEATURE
<222> LOCATION: (6)..(6)
<223> OTHER INFORMATION: Xaa = any amino acid selected from the
      following group: Ala or Arg or Asn or Asp or Cys or Gln or Glu
      or Gly or Ile or Leu or Lys or Met or Pro or Ser or Thr or Tyr or
      Val.

<400> SEQUENCE: 24

His Xaa His Arg His Xaa His
1               5

<210> SEQ ID NO 25
<211> LENGTH: 4
<212> TYPE: PRT
<213> ORGANISM: Artificial Sequence
<220> FEATURE:
<223> OTHER INFORMATION: enterokinase substrate sequence

<400> SEQUENCE: 25

Asp Asp Asp Lys
1

<210> SEQ ID NO 26
<211> LENGTH: 5
<212> TYPE: PRT
<213> ORGANISM: Artificial Sequence
<220> FEATURE:
```

<223> OTHER INFORMATION: enterokinase substrate sequence

<400> SEQUENCE: 26

Asp Asp Asp Asp Lys
1               5

<210> SEQ ID NO 27
<211> LENGTH: 6
<212> TYPE: PRT
<213> ORGANISM: Artificial Sequence
<220> FEATURE:
<223> OTHER INFORMATION: thrombin cleavage site sequence
<220> FEATURE:
<221> NAME/KEY: MISC_FEATURE
<222> LOCATION: (6)..(6)
<223> OTHER INFORMATION: Xaa = any non-acidic amino acid

<400> SEQUENCE: 27

Leu Val Pro Arg Gly Xaa
1               5

<210> SEQ ID NO 28
<211> LENGTH: 5
<212> TYPE: PRT
<213> ORGANISM: Artificial Sequence
<220> FEATURE:
<223> OTHER INFORMATION: Factor Xa protease cleavage site sequence
<220> FEATURE:
<221> NAME/KEY: MISC_FEATURE
<222> LOCATION: (5)..(5)
<223> OTHER INFORMATION: Xaa = any amino acid except proline or arginine

<400> SEQUENCE: 28

Ile Glu Gly Arg Xaa
1               5

<210> SEQ ID NO 29
<211> LENGTH: 5
<212> TYPE: PRT
<213> ORGANISM: Artificial Sequence
<220> FEATURE:
<223> OTHER INFORMATION: Factor Xa protease cleavage site sequence
<220> FEATURE:
<221> NAME/KEY: MISC_FEATURE
<222> LOCATION: (5)..(5)
<223> OTHER INFORMATION: Xaa = any amino acid except proline or arginine

<400> SEQUENCE: 29

Ile Asp Gly Arg Xaa
1               5

<210> SEQ ID NO 30
<211> LENGTH: 5
<212> TYPE: PRT
<213> ORGANISM: Artificial Sequence
<220> FEATURE:
<223> OTHER INFORMATION: Factor Xa protease cleavage site sequence
<220> FEATURE:
<221> NAME/KEY: MISC_FEATURE
<222> LOCATION: (5)..(5)
<223> OTHER INFORMATION: Xaa = any amino acid except proline or arginine

<400> SEQUENCE: 30

Ala Glu Gly Arg Xaa
1               5

<210> SEQ ID NO 31
<211> LENGTH: 6
<212> TYPE: PRT

```
<213> ORGANISM: Artificial Sequence
<220> FEATURE:
<223> OTHER INFORMATION: antigenic domain sequence
<220> FEATURE:
<221> NAME/KEY: MISC_FEATURE
<222> LOCATION: (4)..(5)
<223> OTHER INFORMATION: Xaa = independent amino acid residues

<400> SEQUENCE: 31

Asp Tyr Lys Xaa Xaa Asp
1               5

<210> SEQ ID NO 32
<211> LENGTH: 8
<212> TYPE: PRT
<213> ORGANISM: Artificial Sequence
<220> FEATURE:
<223> OTHER INFORMATION: linking sequence with enterokinase linkable
      site
<220> FEATURE:
<221> NAME/KEY: MISC_FEATURE
<222> LOCATION: (4)..(5)
<223> OTHER INFORMATION: Xaa = independent amino acid residues
<220> FEATURE:
<221> NAME/KEY: MISC_FEATURE
<222> LOCATION: (7)..(7)
<223> OTHER INFORMATION: Xaa = Asp

<400> SEQUENCE: 32

Asp Tyr Lys Xaa Xaa Asp Xaa Lys
1               5

<210> SEQ ID NO 33
<211> LENGTH: 5
<212> TYPE: PRT
<213> ORGANISM: Artificial Sequence
<220> FEATURE:
<223> OTHER INFORMATION: antigenic domain sequence
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (4)..(5)
<223> OTHER INFORMATION: Xaa = any amino acid

<400> SEQUENCE: 33

Asp Xaa Tyr Xaa Xaa
1               5

<210> SEQ ID NO 34
<211> LENGTH: 8
<212> TYPE: PRT
<213> ORGANISM: Artificial Sequence
<220> FEATURE:
<223> OTHER INFORMATION: linking sequence with enterokinase linkable
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (4)..(5)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = Asp

<400> SEQUENCE: 34

Asp Xaa Tyr Xaa Xaa Asp Xaa Lys
```

```
<210> SEQ ID NO 35
<211> LENGTH: 21
<212> TYPE: PRT
<213> ORGANISM: Artificial Sequence
<220> FEATURE:
<223> OTHER INFORMATION: Invented sequence
<220> FEATURE:
<221> NAME/KEY: MISC_FEATURE
<222> LOCATION: (1)..(1)
<223> OTHER INFORMATION: X = at least one amino acid
<220> FEATURE:
<221> NAME/KEY: MISC_FEATURE
<222> LOCATION: (7)..(8)
<223> OTHER INFORMATION: X = at least one amino acid
<220> FEATURE:
<221> NAME/KEY: MISC_FEATURE
<222> LOCATION: (14)..(15)
<223> OTHER INFORMATION: X = at least one amino acid
<220> FEATURE:
<221> NAME/KEY: MISC_FEATURE
<222> LOCATION: (21)..(21)
<223> OTHER INFORMATION: X = at least one amino acid
<220> FEATURE:
<221> NAME/KEY: MISC_FEATURE
<222> LOCATION: (4)..(5)
<223> OTHER INFORMATION: X = an amino acid
<220> FEATURE:
<221> NAME/KEY: MISC_FEATURE
<222> LOCATION: (11)..(12)
<223> OTHER INFORMATION: X = an amino acid
<220> FEATURE:
<221> NAME/KEY: MISC_FEATURE
<222> LOCATION: (18)..(19)
<223> OTHER INFORMATION: X = an amino acid
<220> FEATURE:
<221> NAME/KEY: MISC_FEATURE
<222> LOCATION: (1)..(7)
<223> OTHER INFORMATION: the group of amino acids in positions 1
      through 7 may be either present or absent
<220> FEATURE:
<221> NAME/KEY: MISC_FEATURE
<222> LOCATION: (8)..(14)
<223> OTHER INFORMATION: the group of amino acids in positions 8
      through 14 may be either present or absent
<220> FEATURE:
<221> NAME/KEY: MISC_FEATURE
<222> LOCATION: (15)..(21)
<223> OTHER INFORMATION: the group of amino acids in positions 15
      through 21 may be either present or absent

<400> SEQUENCE: 35

Xaa Tyr Lys Xaa Xaa Asp Xaa Xaa Tyr Lys Xaa Xaa Asp Xaa Xaa Tyr
1               5                   10                  15

Lys Xaa Xaa Asp Xaa
            20

<210> SEQ ID NO 36
<211> LENGTH: 6
<212> TYPE: PRT
<213> ORGANISM: Artificial Sequence
<220> FEATURE:
<223> OTHER INFORMATION: Invented sequence
<220> FEATURE:
<221> NAME/KEY: MISC_FEATURE
<222> LOCATION: (1)..(1)
<223> OTHER INFORMATION: X = at least one amino acid
<220> FEATURE:
<221> NAME/KEY: MISC_FEATURE
<222> LOCATION: (4)..(5)
<223> OTHER INFORMATION: X = an amino acid

<400> SEQUENCE: 36
```

```
Xaa Tyr Lys Xaa Xaa Asp
1               5

<210> SEQ ID NO 37
<211> LENGTH: 8
<212> TYPE: PRT
<213> ORGANISM: Artificial Sequence
<220> FEATURE:
<223> OTHER INFORMATION: Invented sequence
<220> FEATURE:
<221> NAME/KEY: MISC_FEATURE
<222> LOCATION: (1)..(1)
<223> OTHER INFORMATION: X = at least one amino acid
<220> FEATURE:
<221> NAME/KEY: MISC_FEATURE
<222> LOCATION: (4)..(5)
<223> OTHER INFORMATION: X = an amino acid
<220> FEATURE:
<221> NAME/KEY: MISC_FEATURE
<222> LOCATION: (7)..(7)
<223> OTHER INFORMATION: X = Asp

<400> SEQUENCE: 37

Xaa Tyr Lys Xaa Xaa Asp Xaa Lys
1               5

<210> SEQ ID NO 38
<211> LENGTH: 5
<212> TYPE: PRT
<213> ORGANISM: Artificial Sequence
<220> FEATURE:
<223> OTHER INFORMATION: Invented sequence
<220> FEATURE:
<221> NAME/KEY: MISC_FEATURE
<222> LOCATION: (1)..(2)
<223> OTHER INFORMATION: X = an amino acid
<220> FEATURE:
<221> NAME/KEY: MISC_FEATURE
<222> LOCATION: (4)..(4)
<223> OTHER INFORMATION: X = Asp

<400> SEQUENCE: 38

Xaa Xaa Asp Xaa Lys
1               5

<210> SEQ ID NO 39
<211> LENGTH: 23
<212> TYPE: PRT
<213> ORGANISM: Artificial Sequence
<220> FEATURE:
<223> OTHER INFORMATION: Invented sequence
<220> FEATURE:
<221> NAME/KEY: MISC_FEATURE
<222> LOCATION: (1)..(1)
<223> OTHER INFORMATION: X = at least one amino acid
<220> FEATURE:
<221> NAME/KEY: MISC_FEATURE
<222> LOCATION: (7)..(8)
<223> OTHER INFORMATION: X = at least one amino acid
<220> FEATURE:
<221> NAME/KEY: MISC_FEATURE
<222> LOCATION: (14)..(14)
<223> OTHER INFORMATION: X = at least one amino acid
<220> FEATURE:
<221> NAME/KEY: MISC_FEATURE
<222> LOCATION: (16)..(16)
<223> OTHER INFORMATION: X = at least one amino acid
<220> FEATURE:
<221> NAME/KEY: MISC_FEATURE
<222> LOCATION: (4)..(5)
<223> OTHER INFORMATION: X = an amino acid
<220> FEATURE:
<221> NAME/KEY: MISC_FEATURE
<222> LOCATION: (11)..(12)
```

```
<223> OTHER INFORMATION: X = an amino acid
<220> FEATURE:
<221> NAME/KEY: MISC_FEATURE
<222> LOCATION: (19)..(20)
<223> OTHER INFORMATION: X = an amino acid
<220> FEATURE:
<221> NAME/KEY: MISC_FEATURE
<222> LOCATION: (15)..(15)
<223> OTHER INFORMATION: X is at least one amino acid or a combination
      of multiple or alternating histidine residues, said combination
      comprising His-Gly-His, or -(His-X)m-, wherein m is 1 to 6 and
      X is selected from the group consisting of Ala, Arg, Asn, Asp,
      Cys, Gln, Glu, Gly, His, Ile, Leu, Lys, Met, Phe, Pro, Ser, Thr,
      Trp, Tyr and Val
<220> FEATURE:
<221> NAME/KEY: MISC_FEATURE
<222> LOCATION: (22)..(22)
<223> OTHER INFORMATION: X = Asp
<220> FEATURE:
<221> NAME/KEY: MISC_FEATURE
<222> LOCATION: (1)..(7)
<223> OTHER INFORMATION: the group of amino acids in positions 1
      through 7 may be either present or absent
<220> FEATURE:
<221> NAME/KEY: MISC_FEATURE
<222> LOCATION: (8)..(14)
<223> OTHER INFORMATION: the group of amino acids in positions 8
      through 14 may be either present or absent

<400> SEQUENCE: 39

Xaa Tyr Lys Xaa Xaa Asp Xaa Xaa Tyr Lys Xaa Xaa Asp Xaa Xaa Xaa
1               5                   10                  15

Tyr Lys Xaa Xaa Asp Xaa Lys
            20

<210> SEQ ID NO 40
<211> LENGTH: 21
<212> TYPE: PRT
<213> ORGANISM: Artificial Sequence
<220> FEATURE:
<223> OTHER INFORMATION: Invented sequence
<220> FEATURE:
<221> NAME/KEY: MISC_FEATURE
<222> LOCATION: (4)..(5)
<223> OTHER INFORMATION: X = an amino acid
<220> FEATURE:
<221> NAME/KEY: MISC_FEATURE
<222> LOCATION: (10)..(11)
<223> OTHER INFORMATION: X = an amino acid
<220> FEATURE:
<221> NAME/KEY: MISC_FEATURE
<222> LOCATION: (17)..(18)
<223> OTHER INFORMATION: X = an amino acid
<220> FEATURE:
<221> NAME/KEY: MISC_FEATURE
<222> LOCATION: (13)..(13)
<223> OTHER INFORMATION: X is at least one amino acid or a combination
      of multiple or alternating histidine residues, said combination
      comprising His-Gly-His, or -(His-X)m-, wherein m is 1 to 6 and X
      is selected from the group consisting of Ala, Arg, Asn, Asp, Cys,
      Gln, Glu, Gly, His, Ile, Leu, Lys, Met, Phe, Pro, Ser, Thr, Trp,
      Tyr and Val
<220> FEATURE:
<221> NAME/KEY: MISC_FEATURE
<222> LOCATION: (20)..(20)
<223> OTHER INFORMATION: X = Asp
<220> FEATURE:
<221> NAME/KEY: MISC_FEATURE
<222> LOCATION: (1)..(12)
<223> OTHER INFORMATION: the group of amino acids in positions 1
      through 12 is present at least once
<220> FEATURE:
<221> NAME/KEY: MISC_FEATURE
<222> LOCATION: (7)..(12)
<223> OTHER INFORMATION: the group of amino acids in positions 7
      through 12 may be repeated any number of times
```

```
<400> SEQUENCE: 40

Asp Tyr Lys Xaa Xaa Asp Asp Tyr Lys Xaa Xaa Asp Xaa Asp Tyr Lys
1               5                   10                  15

Xaa Xaa Asp Xaa Lys
            20

<210> SEQ ID NO 41
<211> LENGTH: 12
<212> TYPE: PRT
<213> ORGANISM: Artificial Sequence
<220> FEATURE:
<223> OTHER INFORMATION: Invented sequence
<220> FEATURE:
<221> NAME/KEY: MISC_FEATURE
<222> LOCATION: (4)..(5)
<223> OTHER INFORMATION: X = an amino acid
<220> FEATURE:
<221> NAME/KEY: MISC_FEATURE
<222> LOCATION: (10)..(11)
<223> OTHER INFORMATION: X = an amino acid
<220> FEATURE:
<221> NAME/KEY: MISC_FEATURE
<222> LOCATION: (1)..(12)
<223> OTHER INFORMATION: the group of amino acids in positions 1
      through 12 is present at least once
<220> FEATURE:
<221> NAME/KEY: MISC_FEATURE
<222> LOCATION: (7)..(12)
<223> OTHER INFORMATION: the group of amino acids in positions 7
      through 12 may be repeated any number of times

<400> SEQUENCE: 41

Asp Tyr Lys Xaa Xaa Asp Asp Tyr Lys Xaa Xaa Asp
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Invented sequence
<220> FEATURE:
<221> NAME/KEY: MISC_FEATURE
<222> LOCATION: (2)..(2)
<223> OTHER INFORMATION: X = an amino acid
<220> FEATURE:
<221> NAME/KEY: MISC_FEATURE
<222> LOCATION: (4)..(4)
<223> OTHER INFORMATION: X = an amino acid
<220> FEATURE:
<221> NAME/KEY: MISC_FEATURE
<222> LOCATION: (8)..(8)
<223> OTHER INFORMATION: X = an amino acid
<220> FEATURE:
<221> NAME/KEY: MISC_FEATURE
<222> LOCATION: (10)..(10)
<223> OTHER INFORMATION: X = an amino acid
<220> FEATURE:
<221> NAME/KEY: MISC_FEATURE
<222> LOCATION: (5)..(5)
<223> OTHER INFORMATION: X = at least one amino acid
<220> FEATURE:
<221> NAME/KEY: MISC_FEATURE
<222> LOCATION: (11)..(11)
<223> OTHER INFORMATION: X = at least one amino acid
<220> FEATURE:
<221> NAME/KEY: MISC_FEATURE
<222> LOCATION: (6)..(6)
<223> OTHER INFORMATION: X is at least one amino acid or a combination
      of multiple or alternating histidine residues, said combination
      comprising His-Gly-His, or -(His-X)m-, wherein m is 1 to 6 and X
      is selected from the group consisting of Ala, Arg, Asn, Asp, Cys,
      Gln, Glu, Gly, His, Ile, Leu, Lys, Met, Phe, Pro, Ser, Thr, Trp,
```

```
        Tyr and Val
<220> FEATURE:
<221> NAME/KEY: MISC_FEATURE
<222> LOCATION: (13)..(13)
<223> OTHER INFORMATION: X is an aspartate
<220> FEATURE:
<221> NAME/KEY: MISC_FEATURE
<222> LOCATION: (1)..(5)
<223> OTHER INFORMATION: the group of amino acids in positions 1
      through 5 may be absent, present once, or repeated any number of
      times

<400> SEQUENCE: 42

Asp Xaa Tyr Xaa Xaa Xaa Asp Xaa Tyr Xaa Xaa Asp Xaa Lys
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Invented sequence
<220> FEATURE:
<221> NAME/KEY: MISC_FEATURE
<222> LOCATION: (2)..(2)
<223> OTHER INFORMATION: X = an amino acid
<220> FEATURE:
<221> NAME/KEY: MISC_FEATURE
<222> LOCATION: (4)..(4)
<223> OTHER INFORMATION: X = an amino acid
<220> FEATURE:
<221> NAME/KEY: MISC_FEATURE
<222> LOCATION: (7)..(7)
<223> OTHER INFORMATION: X = an amino acid
<220> FEATURE:
<221> NAME/KEY: MISC_FEATURE
<222> LOCATION: (9)..(9)
<223> OTHER INFORMATION: X = an amino acid
<220> FEATURE:
<221> NAME/KEY: MISC_FEATURE
<222> LOCATION: (5)..(5)
<223> OTHER INFORMATION: X = at least one amino acid
<220> FEATURE:
<221> NAME/KEY: MISC_FEATURE
<222> LOCATION: (10)..(10)
<223> OTHER INFORMATION: X = at least one amino acid
<220> FEATURE:
<221> NAME/KEY: MISC_FEATURE
<222> LOCATION: (1)..(10)
<223> OTHER INFORMATION: the group of amino acids in positions 1
      through 10 is present once
<220> FEATURE:
<221> NAME/KEY: MISC_FEATURE
<222> LOCATION: (6)..(10)
<223> OTHER INFORMATION: the group of amino acids in positions 6
      through 10 is repeated any number of times

<400> SEQUENCE: 43

Asp Xaa Tyr Xaa Xaa Asp Xaa Tyr Xaa Xaa
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Invented sequence
<220> FEATURE:
<221> NAME/KEY: MISC_FEATURE
<222> LOCATION: (1)..(1)
<223> OTHER INFORMATION: X = an amino acid
<220> FEATURE:
<221> NAME/KEY: MISC_FEATURE
<222> LOCATION: (5)..(6)
<223> OTHER INFORMATION: X = an amino acid
```

```
<220> FEATURE:
<221> NAME/KEY: MISC_FEATURE
<222> LOCATION: (11)..(12)
<223> OTHER INFORMATION: X = an amino acid
<220> FEATURE:
<221> NAME/KEY: MISC_FEATURE
<222> LOCATION: (2)..(13)
<223> OTHER INFORMATION: the group of amino acids in positions 2
      through 13 is present at least once
<220> FEATURE:
<221> NAME/KEY: MISC_FEATURE
<222> LOCATION: (8)..(13)
<223> OTHER INFORMATION: the group of amino acids in positions 8
      through 13 may be repeated any number of times

<400> SEQUENCE: 44

Xaa Asp Tyr Lys Xaa Xaa Asp Asp Tyr Lys Xaa Xaa Asp
1               5                   10

<210> SEQ ID NO 45
<211> LENGTH: 22
<212> TYPE: PRT
<213> ORGANISM: Artificial Sequence
<220> FEATURE:
<223> OTHER INFORMATION: Invented sequence
<220> FEATURE:
<221> NAME/KEY: MISC_FEATURE
<222> LOCATION: (1)..(1)
<223> OTHER INFORMATION: X = an amino acid
<220> FEATURE:
<221> NAME/KEY: MISC_FEATURE
<222> LOCATION: (5)..(6)
<223> OTHER INFORMATION: X = an amino acid
<220> FEATURE:
<221> NAME/KEY: MISC_FEATURE
<222> LOCATION: (11)..(12)
<223> OTHER INFORMATION: X = an amino acid
<220> FEATURE:
<221> NAME/KEY: MISC_FEATURE
<222> LOCATION: (18)..(19)
<223> OTHER INFORMATION: X = an amino acid
<220> FEATURE:
<221> NAME/KEY: MISC_FEATURE
<222> LOCATION: (14)..(14)
<223> OTHER INFORMATION: X is at least one amino acid or a combination
      of multiple or alternating histidine residues, said combination
      comprising His-Gly-H is, or -(His-X)m-, wherein m is 1 to 6 and X
      is selected from the group consisting of Ala, Arg, Asn, Asp, Cys,
      Gln, Glu, Gly, His, Ile, Leu, Lys, Met, Phe, Pro, Ser, Thr, Trp,
      Tyr and Val
<220> FEATURE:
<221> NAME/KEY: MISC_FEATURE
<222> LOCATION: (21)..(21)
<223> OTHER INFORMATION: X = an Asp
<220> FEATURE:
<221> NAME/KEY: MISC_FEATURE
<222> LOCATION: (2)..(13)
<223> OTHER INFORMATION: the group of amino acids in positions 2
      through 13 is present at least once
<220> FEATURE:
<221> NAME/KEY: MISC_FEATURE
<222> LOCATION: (8)..(13)
<223> OTHER INFORMATION: the group of amino acids in positions 8
      through 13 may be repeated any number of times

<400> SEQUENCE: 45

Xaa Asp Tyr Lys Xaa Xaa Asp Asp Tyr Lys Xaa Xaa Asp Xaa Asp Tyr
1               5                   10                  15

Lys Xaa Xaa Asp Xaa Lys
            20

<210> SEQ ID NO 46
<211> LENGTH: 23
<212> TYPE: PRT
```

-continued

```
<213> ORGANISM: Artificial Sequence
<220> FEATURE:
<223> OTHER INFORMATION: Invented sequence

<400> SEQUENCE: 46

Met Asp Tyr Lys Asp His Asp Gly Asp Tyr Lys Asp His Asp Ile Asp
1               5                   10                  15

Tyr Lys Asp Asp Asp Asp Lys
            20
```

US 7,799,561 B2

AFFINITY PEPTIDES AND METHOD FOR PURIFICATION OF RECOMBINANT PROTEINS

REFERENCE TO RELATED APPLICATION

This application is a non-provisional application claiming priority from provisional application Ser. No. 60/388,059, filed Jun. 12, 2002.

FIELD OF THE INVENTION

This invention relates to affinity peptides, fusion proteins containing affinity peptides, genes coding for such proteins, expression vectors and transformed microorganisms containing such genes, and methods for the purification of the fusion proteins.

BACKGROUND OF THE INVENTION

The possibility of preparing hybrid genes by gene technology has opened up new routes for the analysis of recombinant proteins. By linking the coding gene sequence of a desired protein to the coding gene sequence of a protein fragment having a high affinity for a ligand (affinity peptide), it is possible to purify desired recombinant proteins in the form of fusion proteins in one-step using the affinity peptide.

Immobilized metal affinity chromatography (IMAC), also known as metal chelate affinity chromatography (MCAC), is a specialized aspect of affinity chromatography. The principle behind IMAC lies in the fact that many transition metal ions, e.g., nickel, zinc and copper, can coordinate to the amino acids histidine, cysteine, and tryptophan via electron donor groups on the amino acid side chains. To utilize this interaction for chromatographic purposes, the metal ion is typically immobilized onto an insoluble support. This can be done by attaching a chelating group to the chromatographic matrix. Most importantly, to be useful, the metal of choice must have a higher affinity for the matrix than for the compounds to be purified.

In U.S. Pat. No. 4,569,794, Smith et al. disclose the preparation of a fusion protein containing a metal ion-affinity peptide linker and a biologically active polypeptide, expressing the fusion protein, and purifying it using immobilized metal ion chromatography. Because essentially any biologically active polypeptide could be used, this approach enabled the convenient expression and purification of essentially biologically active polypeptide by immobilized metal ion chromatography.

In U.S. Pat. Nos. 5,310,663 and 5,284,933, Dobeli et al. disclose a process for separating a biologically active polypeptide from impurities by producing the desired polypeptide as a fusion protein containing a metal ion-affinity peptide linker comprising 2 to 6 adjacent histidine residues. Although Dobeli et al.'s metal ion-affinity peptide provides greater metal affinity relative to certain of the sequences disclosed by Smith et al., there is some cautionary evidence that proteins containing His-tags may differ from their wild-type counterparts in dimerization/oligomerization properties. For example, Wu and Filutowicz present evidence that the biochemical properties of the pi(30.5) protein of plasmid R6K, a DNA binding protein, were fundamentally altered due to the presence of an N-terminal 6×His-tag. Wu, J. and Filutowicz, M., *Acta Biochim. Pol.*, 46:591-599, 1999. In addition, Rodriguez-Viciana et al. stated that V12 Ras proteins expressed as histidine-tagged fusion proteins exhibited poor biological activity. Rodriguez-Viciana, P., et al., *Cell*, 89:457-67, 1997.

SUMMARY OF THE INVENTION

One aspect of the present invention is a peptide which is relatively hydrophilic, is capable of exhibiting appropriate biological activity, and has a relatively high affinity for coordinating metals. Advantageously, this metal ion-affinity peptide may be incorporated into a fusion protein to enable ready purification of the fusion protein from aqueous solutions by immobilized metal affinity chromatography. In addition to the metal ion-affinity peptide, the fusion protein typically comprises a protein or polypeptide of interest, covalently linked, directly or indirectly, to the metal ion-affinity peptide.

Briefly, therefore, the present invention is directed to a peptide represented by the formula $R_1$-$Sp_1$-(His-$Z_1$-His-Arg-His-$Z_2$-His)-$Sp_2$-$R_2$, wherein (His-$Z_1$-His-Arg-His-$Z_2$-His) (SEQ ID NO: 24) is a metal ion-affinity peptide, $R_1$ is hydrogen, a polypeptide, protein or protein fragment, $Sp_1$ is a covalent bond or a spacer comprising at least one amino acid residue, $R_2$ is hydrogen, a polypeptide, protein or protein fragment, $Sp_2$ is a covalent bond or a spacer comprising at least one amino acid residue, $Z_1$ is an amino acid residue selected from the group consisting of Ala, Arg, Asn, Asp, Gln, Glu, Ile, Lys, Phe, Pro, Ser, Thr, Trp, and Val; and $Z_2$ is an amino acid residue selected from the group consisting of Ala, Arg, Asn, Asp, Cys, Gln, Glu, Gly, Ile, Leu, Lys, Met, Pro, Ser, Thr, Tyr, and Val.

The present invention is further directed to a process for separating a recombinant protein or polypeptide from a liquid mixture wherein the recombinant protein or polypeptide comprises a metal ion-affinity peptide having the sequence His-$Z_1$-His-Arg-His-$Z_2$-His (SEQ ID NO: 24) and $Z_1$ and $Z_2$ are as previously defined. In the process, the mixture is combined with a solid support having immobilized metal ions to bind the recombinant protein or polypeptide, and eluting the fusion protein from the solid support.

The present invention is further directed to vectors and host cells for recombinant expression of the nucleic acid molecules described herein, as well as methods of making such vectors and host cells and for using them for production of the polypeptides or peptides of the present invention by recombinant techniques.

The present invention is further directed to a kit for the expression and/or separation of the recombinant proteins or polypeptides from a mixture wherein the recombinant proteins or polypeptides contain the sequence $R_1$-$Sp_1$-(His-$Z_1$-His-Arg-His-$Z_2$-His)-$Sp_2$-$R_2$ (SEQ ID NO: 24) and $R_1$, $R_2$, $Sp_1$, $Sp_2$, $Z_1$ and $Z_2$ are as previously defined. The kit may comprise, in separate containers, the nucleic acid components to be assembled into a vector encoding for a fusion protein comprising a protein or polypeptide covalently operably linked directly or indirectly to an immobilized metal ion-affinity peptide. In addition, or alternatively, the kit may be comprised of one or more of the following: buffers, enzymes, a chromatography column comprising a resin containing immobilized metal ions and an instructional brochure explaining how to use the kit.

Other objects and advantages of the present invention will become apparent as the detailed description of the invention proceeds.

DETAILED DESCRIPTION OF THE PREFERRED EMBODIMENTS

The present invention generally relates to the expression and purification of recombinant polypeptides, proteins or protein fragments containing a metal ion-affinity peptide. In addition to the metal ion-affinity peptide, the recombinant polypeptides and proteins will typically also contain a target polypeptide, protein or fragment thereof covalently linked to the metal ion-affinity peptide. In one embodiment, the target polypeptide, protein or protein fragment is a biologically active protein or protein fragment. Advantageously, the metal ion-affinity peptide enables the recombinant polypeptides and proteins to be readily purified from a liquid sample by means of metal ion affinity chromatography.

The fusion proteins of this invention are prepared by recombinant DNA methodology. In accordance with the present invention, a gene sequence coding for a desired protein is isolated, synthesized or otherwise obtained and operably linked to a DNA sequence coding for the metal ion-affinity peptide. The hybrid gene containing the gene for a desired protein operably linked to a DNA sequence encoding the metal ion-affinity peptide is referred to as a chimeric gene.

In one embodiment, the metal ion-affinity peptide is covalently linked to the carboxy terminus of the target polypeptide, protein or protein fragment. In another embodiment, the metal ion-affinity peptide is covalently linked to the amino terminus of the target polypeptide, protein or protein fragment. In each of these embodiments, the metal ion-affinity peptide and the target polypeptide, protein or protein fragment may be directly attached by means of a peptide bond or, alternatively, the two may be separated by a linker. When present, the linker may provide other functionality to the recombinant polypeptide, protein or protein fragment.

The recombinant polypeptides, proteins or protein fragments of the present invention are defined by the general formula (I):

$$R_1\text{-}Sp_1\text{-}(His\text{-}Z_1\text{-}His\text{-}Arg\text{-}His\text{-}Z_2\text{-}His)\text{-}Sp_2\text{-}R_2 \qquad (I)$$

wherein (His-$Z_1$-His-Arg-His-$Z_2$-His)(SEQ ID NO: 24) is a metal ion-affinity peptide; $Z_1$ is an amino acid residue selected from the group consisting of Ala, Arg, Asn, Asp, Gln, Glu, Ile, Lys, Phe, Pro, Ser, Thr, Trp, and Val; and $Z_2$ is an amino acid residue selected from the group consisting of Ala, Arg, Asn, Asp, Cys, Gln, Glu, Gly, Ile, Leu, Lys, Met, Pro, Ser, Thr, Tyr and Val. In addition, $R_1$ is hydrogen, a polypeptide, protein or protein fragment, $Sp_1$ is a covalent bond or a spacer comprising at least one amino acid residue, $R_2$ is hydrogen, a polypeptide, protein or protein fragment, $Sp_2$ is a covalent bond or a spacer comprising at least one amino acid residue. Thus, for example, $R_1$ or $R_2$ may comprise a target polypeptide, protein, or protein fragment which is directly or indirectly linked to the metal ion-affinity peptide.

Metal Ion-Affinity Peptide

In one embodiment, the recombinant polypeptide, protein or protein fragment is defined by formula (I), wherein $Z_1$ is an amino acid selected from the group consisting of Ala, Asn, Ile, Lys, Phe, Ser, Thr, and Val; and $Z_2$ is an amino acid selected from the group consisting of Ala, Asn, Gly, Lys, Ser, Thr, Tyr; and $R_1$, $R_2$, $Sp_1$, and $Sp_2$ are as previously defined. Thus, for example, in this embodiment the target polypeptide, protein or protein fragment ($R_1$ or $R_2$) may be at the carboxy or amino terminus of the metal ion-affinity polypeptide. In addition, the target polypeptide, protein or protein fragment ($R_1$ or $R_2$), may be directly fused (when $Sp_1$ or $Sp_2$ is a covalent bond) or separated from the metal ion-affinity polypeptide by a spacer (when $Sp_1$ or $Sp_2$ is one or more amino acid residues) regardless of whether the target polypeptide, protein or protein fragment is fused to the amino or carboxy terminus of the metal ion-affinity polypeptide.

In another embodiment, the recombinant polypeptide, protein or protein fragment is defined by formula (I), wherein $Z_1$ is an amino acid selected from the group consisting of Asn and Lys; and $Z_2$ is an amino acid selected from the group consisting of Gly and Lys; and $R_1$, $R_2$, $Sp_1$, and $Sp_2$ are as previously defined. For example, in one such embodiment, the recombinant polypeptide, protein or protein fragment is defined by formula (I) wherein $Z_1$ is Asn, $Z_2$ is Lys and $R_1$, $R_2$ μl, and $Sp_2$ are as previously defined. By way of further example, in another such embodiment, the recombinant polypeptide, protein or protein fragment is defined by formula (I) wherein $Z_1$ is Lys and $Z_2$ is Gly. In each of these alternatives, the target polypeptide, protein or protein fragment ($R_1$ or $R_2$) may be at the carboxy or amino terminus of the metal ion-affinity polypeptide. In addition, the target polypeptide, protein or protein fragment ($R_1$ or $R_2$), may be directly fused (when $Sp_1$ or $Sp_2$ is a covalent bond) or separated from the metal ion-affinity polypeptide by a spacer (when $Sp_1$ or $Sp_2$ is one or more amino acid residues) regardless of whether the target polypeptide, protein or protein fragment is fused to the amino or carboxy terminus of the metal ion-affinity polypeptide.

In another embodiment, the recombinant polypeptide, protein or protein fragment is defined by formula (I), wherein $Z_1$ is Ile, $Z_2$ is Asn, and $R_1$, $R_2$, $Sp_1$, and $Sp_2$ are as previously defined. Thus, for example, in this embodiment the target polypeptide, protein or protein fragment ($R_1$ or $R_2$) may be at the carboxy or amino terminus of the metal ion-affinity polypeptide. In addition, the target polypeptide, protein or protein fragment ($R_1$ or $R_2$), may be directly fused (when $Sp_1$ or $Sp_2$ is a covalent bond) or separated from the metal ion-affinity polypeptide by a spacer (when $Sp_1$ or $Sp_2$ is one or more amino acid residues) regardless of whether the target polypeptide, protein or protein fragment is fused to the amino or carboxy terminus of the metal ion-affinity polypeptide.

In another embodiment, the recombinant polypeptide, protein or protein fragment is defined by formula (I), wherein $Z_1$ is Thr, $Z_2$ is Ser, and $R_1$, $R_2$, $Sp_1$, and $Sp_2$ are as previously defined. Thus, for example, in this embodiment the target polypeptide, protein or protein fragment ($R_1$ or $R_2$) may be at the carboxy or amino terminus of the metal ion-affinity polypeptide. In addition, the target polypeptide, protein or protein fragment ($R_1$ or $R_2$), may be directly fused (when $Sp_1$ or $Sp_2$ is a covalent bond) or separated from the metal ion-affinity polypeptide by a spacer (when $Sp_1$ or $Sp_2$ is one or more amino acid residues) regardless of whether the target polypeptide, protein or protein fragment is fused to the amino or carboxy terminus of the metal ion-affinity polypeptide.

In another embodiment, the recombinant polypeptide, protein or protein fragment is defined by formula (I), wherein $Z_1$ is Ser, $Z_2$ is Tyr, and $R_1$, $R_2$, $Sp_1$, and $Sp_2$ are as previously defined. Thus, for example, in this embodiment the target polypeptide, protein or protein fragment ($R_1$ or $R_2$) may be at the carboxy or amino terminus of the metal ion-affinity polypeptide. In addition, the target polypeptide, protein or protein fragment ($R_1$ or $R_2$), may be directly fused (when $Sp_1$ or $Sp_2$ is a covalent bond) or separated from the metal ion-affinity polypeptide by a spacer (when $Sp_1$ or $Sp_2$ is one or more amino acid residues) regardless of whether the target polypeptide, protein or protein fragment is fused to the amino or carboxy terminus of the metal ion-affinity polypeptide.

In another embodiment, the recombinant polypeptide, protein or protein fragment is defined by formula (I), wherein $Z_1$ is Val, $Z_2$ is Ala, and $R_1$, $R_2$, $Sp_1$, and $Sp_2$ are as previously defined. Thus, for example, in this embodiment the target polypeptide, protein or protein fragment ($R_1$ or $R_2$) may be at the carboxy or amino terminus of the metal ion-affinity polypeptide. In addition, the target polypeptide, protein or protein fragment ($R_1$ or $R_2$), may be directly fused (when $Sp_1$ or $Sp_2$ is a covalent bond) or separated from the metal ion-affinity polypeptide by a spacer (when $Sp_1$ or $Sp_2$ is one or more amino acid residues) regardless of whether the target polypeptide, protein or protein fragment is fused to the amino or carboxy terminus of the metal ion-affinity polypeptide.

In another embodiment, the recombinant polypeptide, protein or protein fragment is defined by formula (I), wherein $Z_1$ is Ala, $Z_2$ is Lys, and $R_1$, $R_2$, $Sp_1$, and $Sp_2$ are as previously defined. Thus, for example, in this embodiment the target polypeptide, protein or protein fragment ($R_1$ or $R_2$) may be at the carboxy or amino terminus of the metal ion-affinity polypeptide. In addition, the target polypeptide, protein or protein fragment ($R_1$ or $R_2$), may be directly fused (when $Sp_1$ or $Sp_2$ is a covalent bond) or separated from the metal ion-affinity polypeptide by a spacer (when $Sp_1$ or $Sp_2$ is one or more amino acid residues) regardless of whether the target polypeptide, protein or protein fragment is fused to the amino or carboxy terminus of the metal ion-affinity polypeptide.

In a further embodiment, $R_1$ may be a polypeptide which drives expression of the fusion protein and $R_2$ is the target polypeptide, protein or protein fragment. In this embodiment, each of $Sp_1$ and $Sp_2$ may be a covalent bond or a spacer, independently of the other. Thus, for example, $R_1$ may be directly fused to the metal ion-affinity peptide or separated from the metal ion-affinity peptide by a spacer independently of whether $R_2$ is directly fused to the metal ion-affinity peptide or separated from the metal ion-affinity peptide by a spacer; all of these combinations and permutations are contemplated. This type of arrangement is particularly useful when chimeric proteins are constructed which comprise epitopes from two portions of antigenic protein or from two different antigenic proteins. Such chimeric proteins may be useful in vaccine preparations.

In another embodiment, the recombinant polypeptides, proteins or protein fragments of the present invention comprise multiple copies of the metal ion-affinity peptide (His-$Z_1$-His-Arg-His-$Z_2$-His) (SEQ ID NO: 24) wherein $Z_1$ and $Z_2$ are as previously defined. In this embodiment, the additional copies of the metal affinity peptide may occur in either or both of the spacer domains ($Sp_1$ and $Sp_2$) or in either or both of the other domains ($R_1$ and $R_2$) of the recombinant polypeptides, proteins or protein fragments. Thus, for example, in one embodiment a second copy of the metal ion-affinity peptide (His-$Z_1$-His-Arg-His-$Z_2$-His) (SEQ ID NO: 24) wherein $Z_1$ and $Z_2$ are as previously defined is located in one of the spacer domains ($Sp_1$ or $Sp_2$) or other domains ($R_1$ and $R_2$) of the recombinant polypeptides, proteins or protein fragments. By way of further example, in another embodiment two additional copies of the metal ion-affinity peptide (His-$Z_1$-His-Arg-His-$Z_2$-His) (SEQ ID NO: 24) wherein $Z_1$ and $Z_2$ are as previously defined are located in the spacer domains ($Sp_1$ or $Sp_2$) or other domains ($R_1$ and $R_2$) of the recombinant polypeptides, proteins or protein fragments. By way of further example, in another embodiment at least three additional copies of the metal ion-affinity peptide (His-$Z_1$-His-Arg-His-$Z_2$-His) (SEQ ID NO: 24) wherein $Z_1$ and $Z_2$ are as previously defined are located in the spacer domains ($Sp_1$ or $Sp_2$) or other domains ($R_1$ and $R_2$) of the recombinant polypeptides, proteins or protein fragments. In each of these embodiments, the multiple copies of the metal ion-affinity peptide may be separated by one or more amino acid residues (i.e., a spacer) as described herein. Alternatively, in each of these embodiments the multiple copies of the metal ion-affinity peptide may be directly linked to each other without any intervening amino acid residues. Thus, for example, in one such embodiment the recombinant polypeptides, proteins or protein fragments of the present invention may be defined by the general formula (II):

$$R_1\text{-}Sp_1\text{-}(His\text{-}Z_1\text{-}His\text{-}Arg\text{-}His\text{-}Z_2\text{-}His)_t\text{-}Sp_2\text{-}R_2 \quad (II)$$

wherein (His-$Z_1$-His-Arg-His-$Z_2$-His) (SEQ ID NO: 24) is a metal ion-affinity peptide; t is at least 2 and $R_1$, $R_2$, $Z_1$, $Z_2$, $Sp_1$ and $Sp_2$ are as previously defined. By way of further example, in one such embodiment the recombinant polypeptides, proteins or protein fragments of the present invention may be defined by the general formula (III):

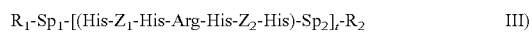
$$R_1\text{-}Sp_1\text{-}[(His\text{-}Z_1\text{-}His\text{-}Arg\text{-}His\text{-}Z_2\text{-}His)\text{-}Sp_2]_t\text{-}R_2 \quad (III)$$

wherein (His-$Z_1$-His-Arg-His-$Z_2$-His) (SEQ ID NO: 24) is a metal ion-affinity peptide; t is at least 2 and $R_1$, $R_2$, $Z_1$, $Z_2$, $Sp_1$ and $Sp_2$ are as previously defined; in addition, each $Sp_2$ of the recombinant polypeptides, proteins or protein fragments corresponding to general formula (III) may be the same or different.

Target Polypeptide, Protein or Protein Fragment

The target polypeptide, protein or protein fragment may be composed of any proteinaceous substance that can be expressed in transformed host cells. Accordingly, the present invention may be beneficially employed to produce substantially any prokaryotic or eukaryotic, simple or conjugated, protein that can be expressed by a vector in a transformed host cell. For example, the target protein may be a) an enzyme, whether oxidoreductase, transferase, hydrolase, lyase, isomerase or ligase;
b) a storage protein, such as ferritin or ovalbumin or a transport protein, such as hemoglobin, serum albumin or ceruloplasmin;
c) a protein that functions in contractile and motile systems such as actin or myosin;
d) any of a class of proteins that serve a protective or defense function, such as the blood protein fibrinogen or a binding protein, such as antibodies or immunoglobulins that bind to and thus neutralize antigens;
e) a hormone such as human Growth Hormone, somatostatin, prolactin, estrone, progesterone, melanocyte, thyrotropin, calcitonin, gonadotropin and insulin;
f) a hormone involved in the immune system, such as interleukin-1, interleukin-2, colony stimulating factor, macrophage-activating factor and interferon;
g) a toxic protein, such as ricin from castor bean or gossypin from cotton linseed;
h) a protein that serves as structural elements such as collagen, elastin, alpha-keratin, glyco-proteins, viral proteins and muco-proteins; or
i) a synthetic protein, defined generally as any sequence of amino acids not occurring in nature.

In general, the target polypeptide, protein or protein fragment may be a constituent of the $R_1$ and $R_2$ moieties of the recombinant polypeptides, proteins or protein fragments corresponding to general formulae (I), (II) and (III).

Genes coding for the various types of protein molecules identified above may be obtained from a variety of prokaryotic or eukaryotic sources, such as plant or animal cells or bacteria cells. The genes can be isolated from the chromosome material of these cells or from plasmids of prokaryotic cells by employing standard, well-known techniques. A variety of naturally occurring and synthesized plasmids having genes coding for many different protein molecules are not commercially available from a variety of sources. The desired DNA also can be produced from mRNA by using the enzyme reverse transcriptase. This enzyme permits the synthesis of DNA from an RNA template.

In one embodiment, $R_1$ may be a protein which enhances expression and $R_2$ is the target polypeptide, protein, or protein fragment. It is well known that the presence of some proteins in a cell result in expression of genes. If a chimeric protein contains an active portion of the protein which prompts or enhances expression of the gene encoding it, greater quantities of the protein may be expressed than if it were not present.

Linker and Other Optional Elements

In one embodiment, the recombinant polypeptide, protein or protein fragment includes a spacer ($Sp_1$ or $Sp_2$) between the metal ion-affinity polypeptide and the target polypeptide, protein or protein fragment. If present, the spacer may simply comprise one or more, e.g., three to ten amino acid residues, separating the metal ion-affinity peptide from the target polypeptide, protein or protein fragment. Alternatively, the spacer may comprise a sequence which imparts other functionality, such as a proteolytic cleavage site, a fusion protein, a secretion sequence (e.g. OmpA or OmpT for E. coli, preprotrypsin for mammalian cells, a-factor for yeast, and melittin for insect cells), a leader sequence for cellular targeting, antibody epitopes, or IRES (internal ribosomal entry sequences) sequences.

In one embodiment, the spacer is selected from among hydrophilic amino acids to increase the hydrophilic character of the recombinant polypeptide, protein or protein fragment. Alternatively, the amino acid(s) of the spacer domain may be selected to impart a desired folding to the recombinant polypeptide, protein or protein fragment thereby increasing accessability to one or more regions of the molecule. For example, the spacer domain may comprise glycine residues which results in a protein folding conformation which allows for improved accessibility to antibodies.

In another embodiment, the spacer comprises a cleavage site which consists of a unique amino acid sequence cleavable by use of a sequence-specific proteolytic agent. Such a site would enable the metal ion-affinity polypeptide to be readily cleaved from the target polypeptide, protein or protein fragment by digestion with a proteolytic agent specific for the amino acids of the cleavage site. Alternatively, the metal ion-affinity peptide may be removed from the desired protein by chemical cleavage using methods known to the art.

When present, the cleavable site may be located at the amino or carboxy terminus of the target peptide. Preferably, the cleavable site is immediately adjacent the desired protein to enable separation of the desired protein from the metal ion-affinity peptide. This cleavable site preferably does not appear in the desired protein. In one embodiment, the cleavable site is located at the amino terminus of the desired protein. If the cleavable site is located at the amino terminus of the desired protein and if there are remaining extraneous amino acids on the desired protein after cleavage with the proteolytic agent, an endopeptidase such as trypsin, clostropain or furin may be utilized to remove these remaining amino acids, thus resulting in a highly purified desired protein. Further examples of proteolytic enzymatic agents useful for cleavage are papain, pepsin, plasmin, thrombin, enterokinase, and the like. Each effects cleavage at a particular amino acid sequence which it recognizes.

Digestion with a proteolytic agent may occur while the fusion protein is still bound to the affinity resin or alternatively, the fusion protein may be eluted from the affinity resin and then digested with the proteolytic agent in order to further purify the desired protein. Preferably, the amino acid sequence of the proteolytic cleavage site is unique, thus minimizing the possibility that the proteolytic agent will cleave the desired protein. In one embodiment, the cleavable site comprises amino acids for an enterokinase, thrombin or a Factor Xa cleavage site.

Enterokinase recognizes several sequences: Asp-Lys; Asp-Asp-Lys; Asp-Asp-Asp-Lys (SEQ ID NO: 25); and Asp-Asp-Asp-Asp-Lys (SEQ ID NO: 26). The only known natural occurrence of Asp-Asp-Asp-Asp-Lys (SEQ ID NO: 26) is in the protein trypsinogen which is a natural substrate for bovine enterokinase and some yeast proteins. As such, by interposing a fragment containing the amino acid sequence Asp-Asp-Asp-Asp-Lys (SEQ ID NO: 26) as a cleavable site between the metal ion-affinity polypeptide and the amino terminus of the target polypeptide, protein or protein fragment, the metal ion-affinity polypeptide can be liberated from the desired protein by use of bovine enterokinase with very little likelihood that this enzyme will cleave any portion of the desired protein itself.

Thrombin cleaves on the carboxy-terminal side of arginine in the following sequence: Leu-Val-Pro-Arg-Gly-X (SEQ ID NO: 27), where X is a non-acidic amino acid. Factor Xa protease (i.e., the activated form of Factor X) cleaves after the Arg in the following sequences: Ile-Glu-Gly-Arg-X (SEQ ID NO: 28), Ile-Asp-Gly-Arg-X (SEQ ID NO: 29), and Ala-Glu-Gly-Arg-X (SEQ ID NO: 30), where X is any amino acid except proline or arginine. A fusion protein comprising the 31 amino-terminal residues of the cII protein, a Factor Xa cleavage site and human β-globin was shown to be cleaved by Factor Xa and generate authentic β-globin. A limitation of the Factor Xa-based fusion systems is the fact that Factor Xa has been reported to cleave at arginine residues that are not present within in the Factor Xa recognition sequence. Lauritzen, C. et al., *Protein Expr. and Purif.*, 5-6:372-378(1991).

While less preferred, other unique amino acid sequences for other cleavable sites may also be employed in the spacer without departing from the spirit or scope of the present invention. For instance, the spacer may be composed, at least in part, of a pair of basic amino acids, i.e., Arg, His or Lys. This sequence is cleaved by kallikreins, a glandular enzyme. Also, the spacer may be composed, at least in part, of Arg-Gly, since it is known that the enzyme thrombin will cleave after the Arg if this residue is followed by Gly.

Regardless of whether a cleavage site is present, the recombinant polypeptide, protein or protein fragment may comprise an antigenic domain in a spacer region ($Sp_1$ or $Sp_2$). For example, in one embodiment of the present invention, the recombinant polypeptide, protein or protein fragment comprises one or multiple copies of an antigenic domain generally corresponding to the FLAG® (Sigma-Aldrich, St. Louis, Mo.) peptide sequence joined to a linking sequence containing a single enterokinase cleavage site. Such antigenic domains generally correspond to the sequence:

$X^{20}$-$(X^1$-Y-K-$X^2$-$X^3$-D-$X^4)_n$-$X^5$-$(X^1$-Y-K-$X^7$-$X^8$-D-$X^9$-K)-$X^{21}$     (SEQ ID NO: 39)

where:

D, Y and K are their representative amino acids;

$X^{20}$ and $X^{21}$ are independently a hydrogen or a covalent bond;

each $X^1$ and $X^4$ is independently a covalent bond or at least one amino acid residue, if other than a covalent bond, preferably at least one amino acid residue selected from the group consisting of aromatic amino acid residues and hydrophilic amino acid residues, more preferably at least one hydrophilic amino acid residue, and still more preferably at least one an aspartate residue;

each $X^2$, $X^3$, $X^7$ and $X^8$ is independently an amino acid residue, preferably an amino acid residue selected from the group consisting of aromatic amino acid residues and hydrophilic amino acid residues, more preferably a hydrophilic amino acid residue, and still more preferably an aspartate residue;

$X^5$ is a covalent bond or a spacer domain comprising at least one amino acid, if other than a covalent bond, preferably a histidine residue, a glycine residue or a combination of multiple or alternating histidine residues, said combination comprising His-Gly-His, or -(His-X)$_m$-, wherein m is 1 to 6 and X is selected from the group consisting of Ala, Arg, Asn, Asp, Cys, Gln, Glu, Gly, His, Ile, Leu, Lys, Met, Phe, Pro, Ser, Thr, Trp, Tyr and Val;

$X^9$ is a covalent bond or D; and n is 0, 1 or 2.

In this embodiment, the amino acid sequence $X^{20}$-(X$^1$-Y-K-X$^2$-X$^3$-D-X$^4$)$_n$ (SEQ ID NO: 35) comprises an antigenic domain -X$^1$-Y-K-X$^2$-X$^3$-D- (SEQ ID NO: 36) joined in tandem which are joined to a linking sequence (X$^1$-Y-K-X$^7$-X$^8$-D-X$^9$-K) (SEQ ID NO: 37). The antigenic domains may be immediately adjacent to each other when n is at least one and $X^4$ is a covalent bond; optionally, $X^4$ may be a spacer domain interposed between the multiple copies of antigenic domains. The linking sequence contains a single enterokinase cleavable site which is represented by the sequence -X$^7$-X$^8$-D-X$^9$-K SEQ ID NO: 38), where $X^7$ and $X^8$ may be an amino acid residue or a covalent bond and $X^9$ is a covalent bond or an aspartate residue. In one embodiment, each $X^7$, $X^8$ and $X^9$ is independently an aspartate residue thus resulting in the enterokinase cleavable site DDDDK (SEQ ID NO: 26) which is preferably located immediately adjacent to the amino terminus of the target peptide. When n is at least one and $X^5$ is a covalent bond, the multiple copies of antigenic domains may be immediately adjacent to the linking sequence; optionally, $X^5$ may be a spacer domain interposed between the linking sequence and the antigenic domains. When each $X^4$ and $X^5$ is independently a spacer domain, it is preferred that the amino acid residue(s) of each $X^4$ and $X^5$ impart one or more desired properties to the antigenic domain; for example, the amino acids of the spacer domain may be selected to impart a desired folding to the identification polypeptide thereby increasing accessibility to the antibody. In another embodiment, the amino acids of the spacer domain $X^4$ and $X^5$ may be selected to impart a desired affinity characteristic such as a combination of multiple or alternating histidine residues capable of chelating to an immobilized metal ion on a resin or other matrix. Furthermore, these desired properties may be designed into other areas of the identification polypeptide; for example, the amino acids represented by $X^2$ and $X^3$ may be selected to impart a desired peptide folding or a desired affinity characteristic for use in affinity purification.

In another embodiment, the spacer comprises multiple copies of an antigenic domain. For example, in one embodiment the spacer may comprise a linking sequence containing a single enterokinase or other cleavage site, or generally correspond to the sequence:

$X^{20}$-(D-Y-K-X$^2$-X$^3$-D)$_n$-X$^5$-(D-Y-K-X$^7$-X$^8$-D-X$^9$-K)-X$^{21}$ (SEQ ID NO: 40)

where:

D, Y, K are their representative amino acids;

$X^{20}$ and $X^{21}$ are independently a hydrogen or a covalent bond;

each $X^2$, $X^3$, $X^7$ and $X^8$ is independently an amino acid residue, preferably an amino acid residue selected from the group consisting of aromatic amino acid residues and hydrophilic amino acid residues, more preferably a hydrophilic amino acid residue, and still more preferably an aspartate residue;

$X^5$ is a covalent bond or a spacer domain comprising at least one amino acid, if other than a covalent bond, preferably a histidine residue, a glycine residue or a combination of multiple or alternating histidine residues, said combination comprising His-Gly-His, or -(His-X)$_m$-, wherein m is 1 to 6 and X is selected from the group consisting of Ala, Arg, Asn, Asp, Cys, Gln, Glu, Gly, His, Ile, Leu, Lys, Met, Phe, Pro, Ser, Thr, Trp, Tyr and Val;

$X^9$ is a covalent bond or an aspartate residue; and n is at least 2.

In this embodiment, the amino acid sequence $X^{20}$-(D-Y-K-X$^2$-X$^3$-D)$_n$ (SEQ ID NO: 41) represents the multiple copies of the antigenic domain D-Y-K-X$^2$-X$^3$-D (SEQ ID NO: 31) in tandem which are joined to a linking sequence (D-Y-K-X$^7$-X$^8$-D-X$^9$-K) (SEQ ID NO: 32). In this embodiment, one antigenic domain is immediately adjacent to another antigenic domain, i.e., no intervening spacer domains, and the multiple copies of the antigenic domain are immediately adjacent to the linking sequence when $X^5$ is a covalent bond. The linking sequence contains a single enterokinase cleavable site which is represented by the sequence -X$^7$-X$^8$-D-X$^9$-K (SEQ ID NO: 38), where $X^7$ and $X^8$ may be a covalent bond or an amino acid residue, preferably an aspartate residue, and $X^9$ is a covalent bond or an aspartate residue. In one embodiment, each $X^7$, $X^8$ and $X^9$ is independently an aspartate residue thus resulting in the enterokinase cleavable site DDDDK (SEQ ID NO: 26) which is preferably adjacent to the amino terminus of the target peptide. Optionally, the multiple copies of the antigenic domain are joined to the linking sequence by a spacer $X^5$ when $X^5$ is at least one amino acid residue. When $X^5$ is a spacer domain, it is preferred that the amino acid residue(s) of $X^5$ impart one or more desired properties to the recombinant polypeptide, protein or protein fragment; for example, the amino acids of the spacer domain may be selected to impart a desired folding to the recombinant polypeptide, protein or protein fragment thereby increasing accessibility to the antibody. In another embodiment, the amino acids of the spacer domain may be selected to impart a desired affinity characteristic such as a combination of multiple or alternating histidine residues capable of chelating to an immobilized metal ion on a resin or other matrix. Furthermore, these desired properties may be designed into other areas of the spacer; for example, the amino acids represented by $X^2$ and $X^3$ may be selected to impart a desired peptide folding or a desired affinity characteristic for use in affinity purification.

When the affinity polypeptide is located at the amino terminus of the target polypeptide, protein or protein fragment, it is often desirable to design the amino acid sequence such that an initiator methionine is present. Accordingly, in one embodiment of the present invention, the recombinant polypeptide, protein or protein fragment comprises multiple copies of an antigenic domain, a linking sequence containing a single enterokinase cleavage site and generally corresponds to the sequence:

$X^{20}$-X$^{10}$-(D-Y-K-X$^2$-X$^3$-D)$_n$-X$^5$-(D-Y-K-X$^7$-X$^8$-D-X$^9$-K)-X$^{21}$ (SEQ ID NO: 45)

where:

D, Y, and K are their representative amino acids;

$X^{20}$ and $X^{21}$ are independently a hydrogen or a covalent bond; $X^{10}$ is a covalent bond or an amino acid, if other than a covalent bond, preferably a methionine residue;

each $X^2$, $X^3$, $X^7$ and $X^8$ is independently an amino acid residue, preferably an amino acid residue selected from the group consisting of aromatic amino acid residues and hydrophilic amino acid residues, more preferably a hydrophilic amino acid residue, and still more preferably an aspartate residue;

$X^5$ is a covalent bond or a spacer domain comprising at least one amino acid, if other than a bond, preferably a histidine residue, a glycine residue or a combination of multiple or alternating histidine residues, said combination comprising His-Gly-His, or -(His-X)$_m$-, wherein m is 1 to 6 and X is selected from the group consisting of Ala, Arg, Asn, Asp, Cys, Gln, Glu, Gly, His, Ile, Leu, Lys, Met, Phe, Pro, Ser, Thr, Trp, Tyr, and Val;

$X^9$ is a covalent bond or an aspartate residue; and n is at least 2.

In this embodiment, the amino acid sequence $X^{20}$-$X^{10}$-(D-Y-K-$X^2$-$X^3$-D)$_n$ (SEQ ID NO: 44) represents the multiple copies of the antigenic domain D-Y-K-$X^2$-$X^3$-D (SEQ ID NO: 31) in tandem which is flanked by a linking sequence (D-Y-K-$X^7$-$X^8$-D-$X^9$-K) (SEQ ID NO: 32) and an initiator amino acid $X^{10}$, preferably methionine. The antigenic domain D-Y-K-$X^2$-$X^3$-D (SEQ ID NO: 31) with an initiator methionine is recognized by the M5® antibody (Sigma-Aldrich, St. Louis, Mo.). In this embodiment, one antigenic domain is immediately adjacent to another antigenic domain, i.e., no intervening spacer domains, and the multiple copies of the antigenic domain are immediately adjacent to the linking sequence when $X^5$ is a covalent bond. The linking sequence contains an enterokinase cleavable site which is represented by the amino acid sequence -$X^7$-$X^8$-D-$X^9$-K, (SEQ ID NO: 38) where $X^7$ and $X^8$ may be a covalent bond or an amino acid residue, preferably an aspartate residue, and $X^9$ is a covalent bond or an aspartate residue. In one embodiment, each $X^7$, $X^8$ and $X^9$ is independently an aspartate residue thus resulting in the enterokinase cleavable site DDDDK (SEQ ID NO: 26) which is preferably adjacent to the amino terminus of the target peptide. Optionally, the multiple copies of the antigenic domain are joined to the linking sequence by a spacer domain $X^5$ when $X^5$ is at least one amino acid residue. When $X^5$ is a spacer domain, it is preferred that the amino acid residue(s) of $X^5$ impart one or more desired properties to the affinity polypeptide; for example, the amino acids of the spacer domain may be selected to impart a desired folding to the recombinant polypeptide, protein or protein fragment thereby increasing accessibility to the antibody. In another embodiment, the amino acids of the spacer domain may be selected to impart a desired affinity characteristic such as a combination of multiple or alternating histidine residues capable of chelating to an immobilized metal ion on a resin or other matrix. Furthermore, these desired properties may be designed into other areas of the affinity polypeptide; for example, the amino acids represented by $X^2$ and $X^3$ may be selected to impart a desired peptide folding or a desired affinity characteristic for use in affinity purification.

In another embodiment of the present invention, the recombinant polypeptide, protein or protein fragment comprises one or more copies of an antigenic sequence, a linking sequence containing a single enterokinase cleavable site and generally corresponds to the sequence:

$X^{20}$-(D-$X^{11}$-Y-$X^{12}$-$X^{13}$)$_n$-$X^{14}$-(D-$X^{11}$-Y-$X^{12}$-$X^{13}$-D-$X^{15}$-K)-$X^{21}$     (SEQ ID NO: 42)

where:

D, Y and K are their representative amino acids;

$X^{20}$ and $X^{21}$ are independently a hydrogen or a covalent bond;

each $X^{11}$ is a covalent bond or an amino acid, preferably Leu;

each $X^{12}$ is an amino acid, preferably selected from the group consisting of aromatic amino acid residues and hydrophilic amino acid residues, more preferably a hydrophilic amino acid residue, and still more preferably an aspartate residue;

each $X^{13}$ is a covalent bond or at least one amino acid, if other than a covalent bond, preferably selected from the group consisting of aromatic amino acid residues and hydrophilic amino acid residues, more preferably a hydrophilic amino acid residue, and still more preferably an aspartate residue;

$X^{14}$ is a covalent bond or a spacer domain comprising at least one amino acid, if other than a covalent bond, preferably a histidine residue, a glycine residue or a combination of multiple or alternating histidine residues, said combination comprising His-Gly-His, or -(His-X)$_m$-, wherein m is 1 to 6 and X is selected from the group consisting of Ala, Arg, Asn, Asp, Cys, Gln, Glu, Gly, His, Ile, Leu, Lys, Met, Phe, Pro, Ser, Thr, Trp, Tyr and Val;

$X^{15}$ is a covalent bond or an aspartate residue; and n is 0 or at least 1.

In this embodiment, when n is at least 2, the amino acid sequence $X^{20}$-(D-$X^{11}$-Y-$X^{12}$-$X^{13}$)$_n$ (SEQ ID NO: 43) constitutes multiple copies of the antigenic domain D-$X^{11}$-Y-$X^{12}$-$X^{13}$ (SEQ ID NO: 33) in tandem which are joined to a linking sequence (D-$X^{11}$-Y-$X^{12}$-$X^{13}$-D-$X^{15}$-K) (SEQ ID NO: 34). Additionally, one antigenic domain may be immediately adjacent to another antigenic domain, i.e., no intervening spacer domains, and the multiple copies of the antigenic domain may be immediately adjacent to the linking sequence when $X^{14}$ is a covalent bond. The linking sequence contains a single enterokinase cleavable site which is represented by the sequence -$X^{12}$-$X^{13}$-D-$X^{15}$-K (SEQ ID NO: 38) where $X^{12}$ and $X^{13}$ may be a covalent bond or an amino acid residue, preferably an aspartate residue, and $X^{15}$ is a covalent bond or an aspartate residue. In one embodiment, each $X^{12}$, $X^{13}$ and $X^{15}$ is independently an aspartate residue thus resulting in the enterokinase cleavable site DDDDK (SEQ ID NO: 26) which is preferably adjacent to the amino terminus of the target peptide. Optionally, when n is at least two, the multiple copies of the antigenic domain are joined to the linking sequence by a spacer $X^{14}$ when $X^{14}$ is at least one amino acid residue. When $X^{14}$ is a spacer domain, it is preferred that the amino acid residue(s) of $X^{14}$ impart one or more desired properties to the recombinant polypeptide, protein or protein fragment; for example, the amino acids of the spacer domain may be selected to impart a desired folding to the recombinant polypeptide, protein or protein fragment thereby increasing accessibility to the antibody. In another embodiment, the amino acids of the spacer domain $X^{14}$ may be selected to impart a desired affinity characteristic such as a combination of multiple or alternating histidine residues capable of chelating to an immobilized metal ion on a resin or other matrix.

In another embodiment of this invention, a spacer (Sp$_1$ or Sp$_2$) comprises the enzyme glutathione-S-transferase of the parasite helminth *Schistosoma japonicum* (SEQ ID NO: 1). The glutathione-S-transferase may, however, be derived from other species including human and other mammalian glutathione-S-transferase. Proteins expressed as fusions with the enzyme glutathione-S-transferase can be purified under non-denaturing conditions by affinity chromatography on immobilized glutathione. Glutathione-agarose beads have a capacity of at least 8 mg fusion protein/ml swollen beads and can be used several times for different preparations of the same fusion protein. Smith, D. B. and Johnson, K. S., *Gene,* 67:31-40, 1988.

In another embodiment of this invention, a spacer (Sp$_1$ or Sp$_2$) comprises a cellulose binding domain (CBD) (SEQ ID NO: 2). CBD's are found in both bacterial and fungal sources and possess a high affinity for the crystalline form of cellulose. This property has been useful for purification of fusion proteins using a cellulose matrix. Fusion proteins have been attached at both the N- and C-terminus of CBD.

In another embodiment of this invention, a spacer ($Sp_1$ or $Sp^2$) comprises the Maltose Binding Protein (MBP) encoded by the malE gene in *E. coli* (SEQ ID NO: 3). MBP has found utility in the formation of chimeric proteins with eukaryotic proteins for expression in bacterial systems. This system permits expression of soluble fusion proteins that can readily be purified on immobilized amylose resin.

In another embodiment of this invention, a spacer ($Sp_1$ or $Sp_2$) comprises Protein A (SEQ ID NO: 4). Protein A is isolated from *Staphylococcus aureus* and binds to the Fc origin of IgG. Fusion proteins containing the IgG binding domains of Protein A can be affinity purified on IgG resins (e.g., IgG Sepharose 6FF (Pharmacia Biotech). The signal sequence of Protein A is functional in *E. coli*. Fusion proteins using Protein A have shown increased stability when expressed both in the cytoplasm and periplasm in *E. coli*.

In another embodiment of this invention, a spacer ($Sp_1$ or $Sp_2$) comprises Protein G (SEQ ID NO: 5). Protein G is similar to Protein A with the difference being that Protein G binds to human serum albumin in addition to IgG. The major disadvantage is that low pH<3.4 is required to elute the fusion protein.

In another embodiment of this invention, a spacer (Spa or $Sp_2$) comprises IgG (SEQ ID NO: 6). Placing the protein of interest on the C-terminal of IgG generates chimeric proteins. This allows purification of the fusion protein using either Protein A or G matrix.

In another embodiment of this invention, a spacer ($Sp_1$ or $Sp_2$) comprises the enzyme chloramphenicol acetyl transferase (CAT) from *E. coli* (SEQ ID NO: 7). CAT is used in the form of a C-terminal fusion. CAT is readily translated in *E. coli* and allows for over-expression of heterologous proteins. Capture of fusion proteins is accomplished using a chloramphenicol matrix.

In another embodiment of this invention, a spacer ($Sp_1$ or $Sp_2$) comprises streptavidin (SEQ ID NO: 8). Streptavidin is used for fusion proteins because of its high affinity and high specificity for biotin. Streptavidin is a neutral protein, free from carbohydrates and sulphydryl groups.

In another embodiment of this invention, a spacer ($Sp_1$ or $Sp_2$) comprises b-galactosidase (SEQ ID NO: 9). b-galactosidase is a enzyme that is utilized as both an N- and C-terminal fusion protein. Fusion proteins containing b-galactosidase sequences can be affinity purified on aminophenyl-b-D-thiogalactosidyl-succinyldiaminohexyl-Sepharose. However, given that C-terminal fusion proteins are usually insoluble, the system has limited use in bacterial systems. N-terminal fusions are soluble in *E. coli*, but due to the large size of b-galactosidase, this system is used more often in eukaryotic gene expression.

In another embodiment of this invention, a spacer ($Sp_1$ or $Sp_2$) comprises the Green Fluorescent Protein (GFP) (SEQ ID NO: 10). GFP is a protein from the jellyfish *Aquorea victorea* and many mutant variations of this protein have been used successfully in most organisms for protein expression. The major use of these types of fusion proteins is for targeting and determining physiological function of the host cell protein.

In another embodiment of this invention, a spacer ($Sp_1$ or $Sp_2$) comprises thioredoxin (SEQ ID NO: 11). Thioredoxin is a relatively small thermostable protein that is easily over-expressed in bacterial systems. Thioredoxin fusion systems are useful in avoiding the formation of inclusion bodies during heterologous gene expression. This has been particularly useful in the expression of mammalian cytokines.

In another embodiment of this invention, a spacer ($Sp_1$ or $Sp_2$) comprises Calmodulin Binding Protein (CBP) (SEQ ID NO: 12). This tag is derived from the C-terminus of skeletal muscle myosin light chain kinase. This small tag is recognized by calmodulin and forms the base of the technology. The tag is translated efficiently and allows for the expression and recovery of N-terminal chimeric genes.

In another embodiment of this invention, a spacer ($Sp_1$ or $Sp_2$) comprises the c-myc epitope sequence Glu-Gln-Lys-Leu-Ile-Ser-Glu-Glu-Asp-Leu (SEQ ID NO: 13). This C-terminal portion of the myc oncogene, which is part of the p53 signaling pathway, has been used as a detection tag for expression of recombinant proteins in mammalian cells.

In another embodiment of this invention, a spacer ($Sp_1$ or $Sp_2$) comprises the HA epitope sequence Tyr-Pro-Tyr-Asp-Val-Tyr-Ala (SEQ ID NO: 14). This detection tag has been utilized for the expression of recombinant proteins in mammalian cells.

In another embodiment of this invention, the spacer ($Sp_1$ or $Sp_2$) comprises a polypeptide possessing an amino acid sequence having at least 70% homology to any one of the amino acid sequences disclosed in SEQ ID NOS:1-14, and retains the same binding characteristics as said amino acid sequence.

DNA sequences encoding the aforementioned proteins which may be employed as spacers ($Sp_1$ or $Sp_2$) are commercially available (e.g., malE gene sequences encoding the MBP are available from New England Biolabs (pMAL-c2 and pMAL-p2); *Schistosoma japonicum* glutathione-S-transferase (GST) gene sequences are available from Pharmacia Biotech (the pGEX series which have GenBank Accession Nos.: U13849 to U13858); β-galactosidase (the lacZ gene product) gene sequences are available from Pharmacia Biotech (pCH110 and pMC1871; GenBank Accession Nos: U13845 and L08936, respectively); sequences encoding the IgG binding domains of Protein A are available from Pharmacia Biotech (pRIT2T; GenBank Accession No. U13864)).

When any of the above listed proteins (including the hinge/Fc domains of human $IgG_1$) are used as spacers, it is not required that the entire protein be used as a spacer. Portions of these proteins may be used as the spacer provided the portion selected is sufficient to permit interaction of a fusion protein containing the portion of the protein used as the spacer with the desired affinity resin.

Expression and Purification

The polypeptides, proteins and protein fragments of the present invention are generally prepared and expressed as a fusion protein using conventional recombinant DNA technology. The fusion protein is thus produced by host cells transformed with the genetic information encoding the fusion protein. The host cells may secrete the fusion protein into the culture media or store it in the cells whereby the cells must be collected and disrupted in order to extract the product. As hosts, *E. coli*, yeast, insect cells, mammalian cells and plants are suitable. Of these two, *E. coli* will typically be the more preferred host for most applications. In one embodiment, the recombinant polypeptides, proteins and protein fragments are produced in a soluble form or secreted from the host.

In general, a chimeric gene is inserted into an expression vector which allows for the expression of the desired fusion protein in a suitable transformed host. The expression vector provides the inserted chimeric gene with the necessary regulatory sequences to control expression in the suitable transformed host.

There are six elements of control expression sequence for proteins which are to be secreted from a host into the medium, while five of these elements apply to fusion proteins expressed intracellularly. These elements in the order they appear in the gene are: a) the promoter region; b) the 5' untranslated region; c) signal sequence; d) the chimeric coding sequence; e) the 3' untranslated region; f) the transcription termination site. Fusion proteins which are not secreted do not contain c), the signal sequence.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, operably linked to the nucleic acid sequence to be expressed. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin, and methotrexate. Nucleic acid encoding a selectable marker can be introduced into a host cell on the same vector as that encoding the metal ion-affinity peptide containing fusion protein or can be introduced on a separate vector. Cells stably transfected with the introduced nucleic acid can be identified by drug selection (e.g., cells that have incorporated the selectable marker gene will survive, while the other cells die). Methods and materials for preparing recombinant vectors, transforming host cells using replicating vectors, and expressing biologically active foreign polypeptides and proteins are generally well known.

The expressed recombinant polypeptides, proteins and protein fragments may be separated from other material present in the secretion media or extraction solution, or from other liquid mixtures, through immobilized metal affinity chromatography ("IMAC"). For example, the culture media containing the secreted recombinant polypeptides, proteins and protein fragments or the cell extracts containing the recombinant polypeptides, proteins and protein fragments may be passed through a column that contains a resin comprising an immobilized metal ion. In IMAC, metal ions are immobilized onto to a solid support, and used to capture proteins comprising a metal chelating peptide. The metal chelating peptide may occur naturally in the protein, or the protein may be a recombinant protein with an affinity tag comprising a metal chelating peptide. Exemplary metal ions include aluminum, cadmium, calcium, cobalt, copper, gallium, iron, nickel, ytterbium and zinc. In one embodiment, the metal ion is preferably nickel, copper, cobalt, or zinc. In another embodiment, the metal ion is nickel. Advantageously, the components of the solution other than recombinant polypeptide, protein or protein fragment freely pass through the column. The immobilized metal, however, chelates or binds the recombinant polypeptides, proteins and protein fragments, thereby separating it from the remaining contents of the liquid mixture in which it was originally contained.

Resins useful for producing immobilized metal ion affinity chromatography (IMAC) columns are available commercially. Examples of resins derivatized with iminodiacetic acid (IDA) are Chelating Sepharose 6B (Pharmacia), Immobilized Iminodiacetic Acid (Pierce), and Iminodiacetic Acid Agarose (Sigma-Aldrich). In addition, Porath has immobilized tris(carboxymethyl)ethylenediamine (TED) on Sepharose 6B and used it to fractionate serum proteins. Porath, J. and Olin, B., *Biochemistry,* 22:1621-1630,1983. Other reports suggest that trisacryl GF2000 and silica can be derivatized with IDA, TED, or aspartic acid, and the resulting materials used in producing IMAC substances.

In one embodiment, the capture ligand is a metal chelate as described in WO 01/81365. More specifically, in this embodiment the capture ligand is a metal chelate derived from metal chelating composition (1):

$$Q-S^1-L-N\begin{matrix}(CH_2)_i-Y\\ \\(CH_2)_i-Z\end{matrix} \qquad (1)$$

wherein

Q is a carrier;

$S^1$ is a spacer;

L is -A-T-CH(X)— or —C(=O)—;

A is an ether, thioether, selenoether, or amide linkage;

T is a bond or substituted or unsubstituted alkyl or alkenyl;

X is —$(CH_2)_k CH_3$, —$(CH_2)_k COOH$, —$(CH_2)_k SO_3H$, —$(CH_2)_k PO_3H_2$, —$(CH_2)_k N(J)_2$, or —$(CH_2)_k P(J)_2$, preferably —$(CH_2)_k COOH$ or —$(CH_2)_k SO_3H$;

k is an integer from 0 to 2;

J is hydrocarbyl or substituted hydrocarbyl;

Y is —COOH, —H, —$SO_3H$, —$PO_3H_2$, —$N(J)_2$, or —$P(J)_2$, preferably, —COOH;

Z is —COOH, —H, —$SO_3H$, —$PO_3H_2$, —$N(J)_2$, or —$P(J)_2$, preferably, —COOH; and i is an integer from 0 to 4, preferably 1 or 2.

In general, the carrier, Q, may comprise any solid or soluble material or compound capable of being derivatized for coupling. Solid (or insoluble) carriers may be selected from a group including agarose, cellulose, methacrylate copolymers, polystyrene, polypropylene, paper, polyamide, polyacrylonitrile, polyvinylidene, polysulfone, nitrocellulose, polyester, polyethylene, silica, glass, latex, plastic, gold, iron oxide and polyacrylamide, but may be any insoluble or solid compound able to be derivatized to allow coupling of the remainder of the composition to the carrier, Q. Soluble carriers include proteins, nucleic acids including DNA, RNA, and oligonucleotides, lipids, liposomes, synthetic soluble polymers, proteins, polyamino acids, albumin, antibodies, enzymes, streptavidin, peptides, hormones, chromogenic dyes, fluorescent dyes, flurochromes or any other detection molecule, drugs, small organic compounds, polysaccharides and any other soluble compound able to be derivatized for coupling the remainder of the composition to the carrier, Q. In one embodiment, the carrier, Q, is the container of the present invention. In another embodiment, the carrier, Q, is a body provided within the container of the present invention.

The spacer, $S^1$, which flanks the carrier comprises a chain of atoms which may be saturated or unsaturated, substituted or unsubstituted, linear or cyclic, or straight or branched. Typically, the chain of atoms defining the spacer, $S^1$, will consist of no more than about 25 atoms; stated another way, the backbone of the spacer will consist of no more than about 25 atoms. More preferably, the chain of atoms defining the spacer, $S^1$, will consist of no more than about 15 atoms, and still more preferably no more than about 12 atoms. The chain of atoms defining the spacer, $S^1$, will typically be selected from the group consisting of carbon, oxygen, nitrogen, sulfur, selenium, silicon and phosphorous and preferably from the group consisting of carbon, oxygen, nitrogen, sulfur and selenium. In addition, the chain atoms may be substituted or unsubstituted with atoms other than hydrogen such as hydroxy, keto (=O), or acyl such as acetyl. Thus, the chain may optionally include one or more ether, thioether, selenoether, amide, or amine linkages between hydrocarbyl or substituted hydrocarbyl regions. Exemplary spacers, $S^1$, include methylene, alkyleneoxy (—$(CH_2)_aO$—), alkylenethioether (—$(CH_2)_aS$—), alkyleneselenoether (—$(CH_2)_aSe$—), alkyleneamide (—$(CH_2)_aNR^1(C=O)$—), alkylenecarbonyl (—$(CH_2)_aCO$—), and combinations thereof wherein a is generally from 1 to about 20 and $R^1$ is hydrogen or hydrocarbyl, preferably alkyl. In one embodiment, the spacer, $S^1$, is a hydrophilic, neutral structure and does not contain any amine linkages or substituents or other linkages or substituents which could become electrically charged during the purification of a polypeptide.

As noted above, the linker, L, may be -A-T-CH(X)— or —C(=O)—. When L is -A-T-CH(X)—, the chelating composition corresponds to the formula:

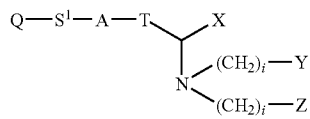

wherein Q, $S_1$, A, T, X, Y, and Z are as previously defined. In this embodiment, the ether (—O—), thioether (—S—), selenoether (—Se—) or amide ((—$NR^1(C=O)$—) or (—$(C=O)NR^1$—) wherein $R^1$ is hydrogen or hydrocarbyl) linkage is separated from the chelating portion of the molecule by a substituted or unsubstituted alkyl or alkenyl region. If other than a bond, T is preferably substituted or unsubstituted $C_1$ to $C_6$ alkyl or substituted or unsubstituted $C_2$ to $C_6$ alkenyl. More preferably, A is —S—, T is —$(CH_2)_n$—, and n is an integer from 0 to 6, typically 0 to 4, and more typically 0, 1 or 2.

When L is —C(=O)—, the chelating composition corresponds to the formula:

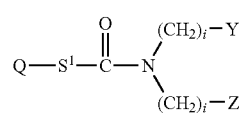

wherein Q, $S^1$, i, Y, and Z are as previously defined.

In one embodiment, the sequence —$S^1$-L-, in combination, is a chain of no more than about 35 atoms selected from the group consisting of carbon, oxygen, sulfur, selenium, nitrogen, silicon and phosphorous, more preferably only carbon, oxygen sulfur and nitrogen, and still more preferably only carbon, oxygen and sulfur. To reduce the prospects for nonspecific binding, nitrogen, when present, is preferably in the form of an amide moiety. In addition, if the carbon chain atoms are substituted with anything other than hydrogen, they are preferably substituted with hydroxy or keto. In one embodiment, L comprises a portion (sometimes referred to as a fragment or residue) derived from an amino acid such as cystine, homocystine, cysteine, homocysteine, aspartic acid, cysteic acid or an ester thereof such as the methyl or ethyl ester thereof.

Exemplary chelating compositions corresponding to formula 1 include the following:

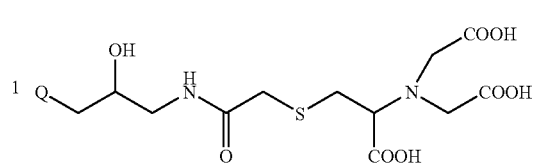

1-1

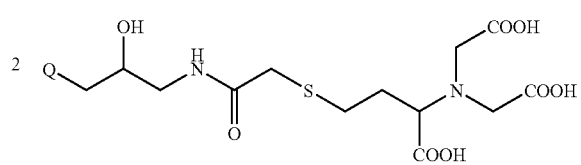

1-2

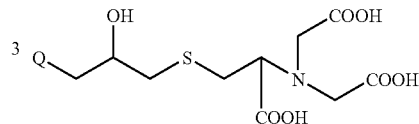

1-3

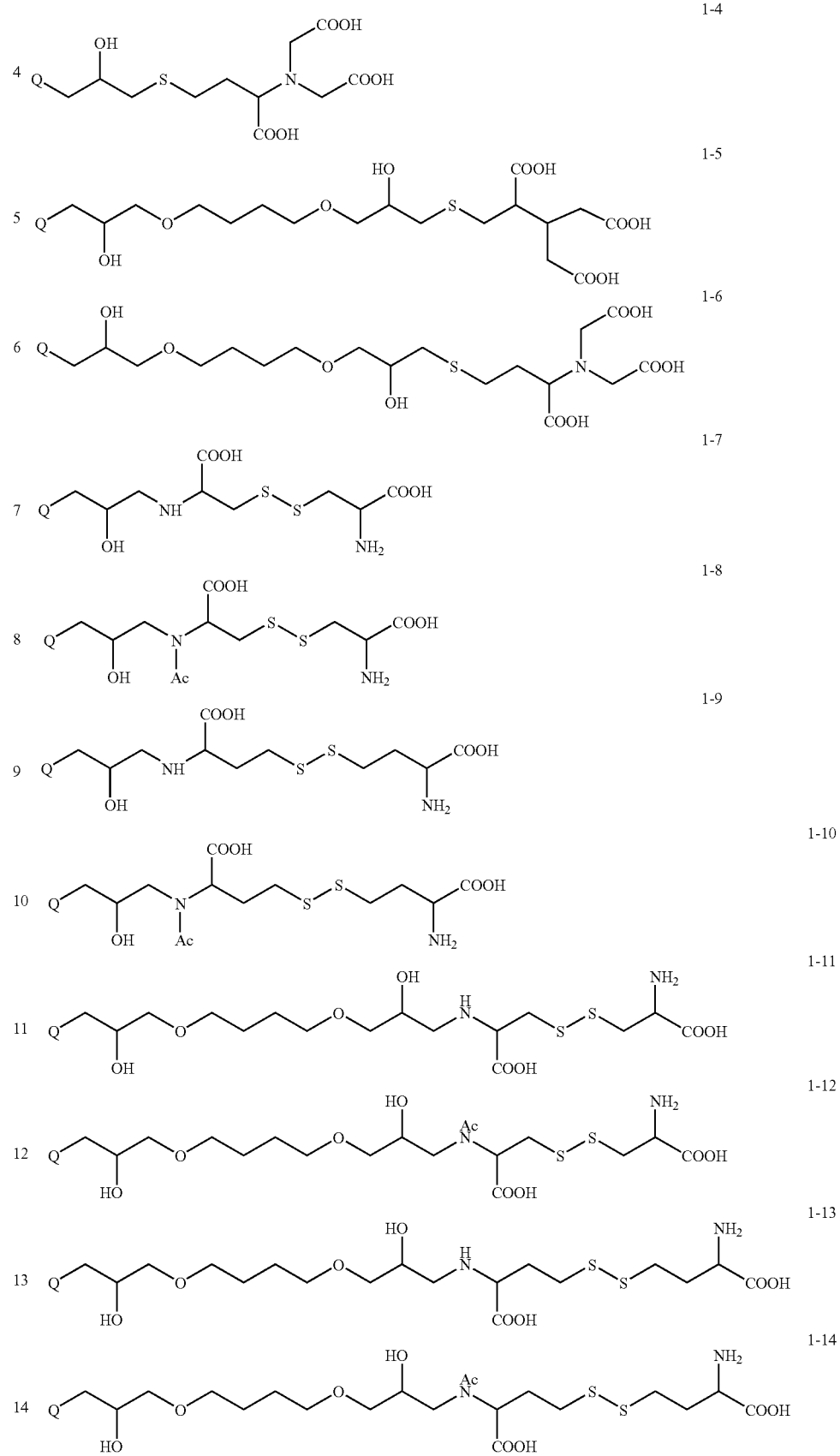

-continued
1-15
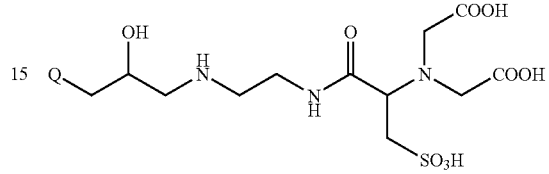
1-16
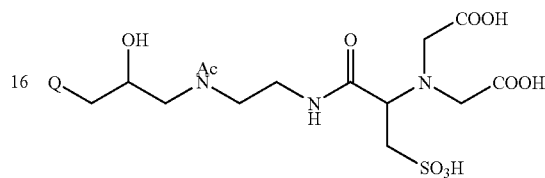
1-17
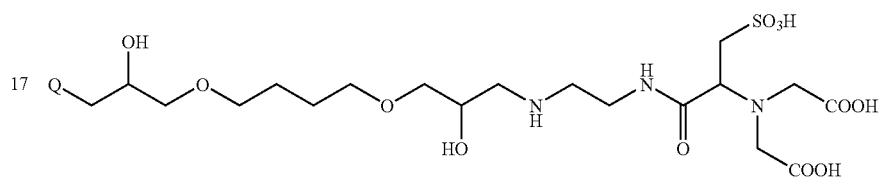
1-18
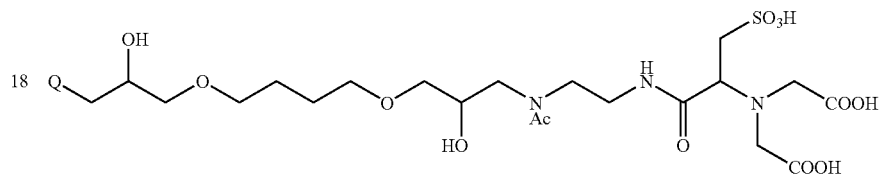
1-19
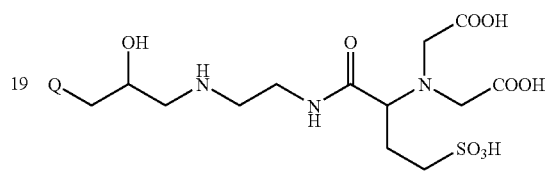
1-20
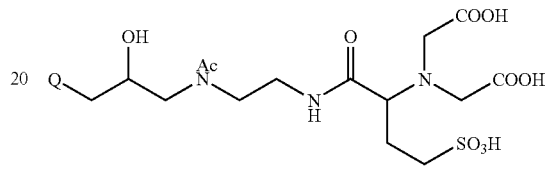
1-21
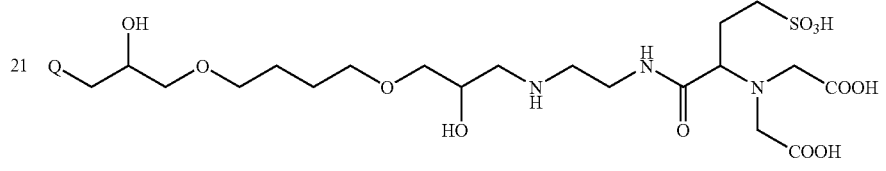
1-22
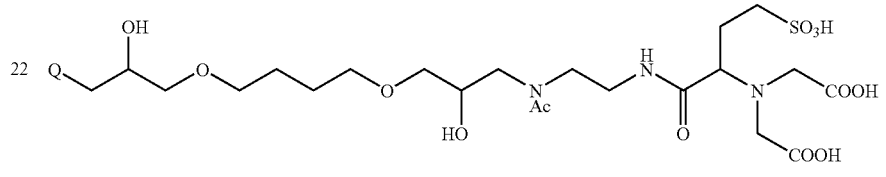
1-23
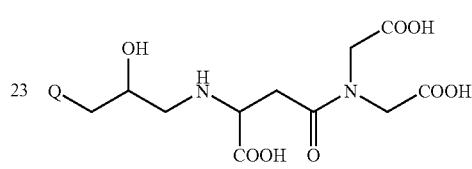

-continued

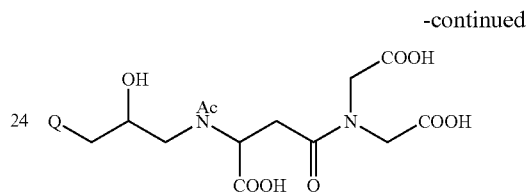

1-24

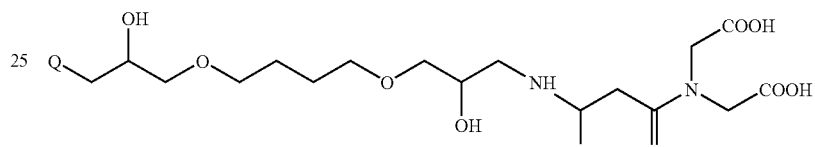

1-25

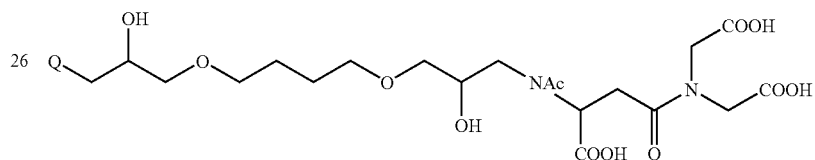

1-26 wherein Q is a carrier and Ac is acetyl.

In another embodiment, the capture ligand is a metal chelate of the type described in U.S. Pat. No. 5,047,513. More specifically, in this embodiment the capture ligand is a metal chelate derived from nitrilotriacetic acid derivatives of the formula

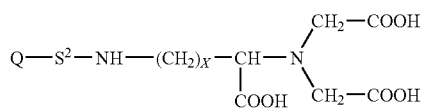

wherein $S^2$ is $-O-CH_2-CH(OH)-CH_2-$ or $-O-CO-$ and x is 2, 3 or 4. In this embodiment, the nitrilotriacetic acid derivative is immobilized on any of the previously described carriers, Q.

In these embodiments in which the capture ligand is a metal chelate as described in WO 01/81365 or U.S. Pat. No. 5,047,513, the metal chelate may contain any of the metal ions previously described in connection with IMAC. In one embodiment, the metal chelate comprises a metal ion selected from among nickel ($Ni^{2+}$), zinc ($Zn^{2+}$), copper ($Cu^{2+}$), iron ($Fe^{3+}$), cobalt ($Co^{2+}$), calcium ($Ca^{2+}$), aluminum ($Al^{3+}$), magnesium ($Mg^{2+}$), and manganese ($Mn^{2+}$). In another embodiment, the metal chelate comprises nickel ($Ni^{2+}$).

Another common purification technique that can be used in the context of the present invention is the use of an immunogenic capture system where the recombinant polypeptide, protein or protein fragment comprises an antigenic domain in a spacer region ($Sp_1$ or $Sp_2$). Any of the previously described antigenic systems comprising the spacer may be used for this purpose. In such systems, an epitope tag on a protein or peptide allows the protein to which it is attached to be purified based upon the affinity of the epitope tag for a corresponding ligand (e.g., antibody) immobilized on a support. One example of such a tag is the sequence Asp-Tyr-Lys-Asp-Asp-Asp-Asp-Lys (SEQ ID NO: 15), or DYKDDDDK (SEQ ID NO: 15); antibodies having specificity for this sequence are sold by Sigma-Aldrich (St. Louis, Mo.) under the FLAG® trademark. Another example of such a tag is the sequence Asp-Leu-Tyr-Asp-Asp-Asp-Asp-Lys (SEQ ID NO: 16), or DLYDDDDK (SEQ ID NO: 16); antibodies having specificity for this sequence are sold by Invitrogen (Carlsbad, Ca.). Another example of such a tag is the 3X FLAG® sequence Met-Asp-Tyr-Lys-Asp-His-Asp-Gly-Asp-Tyr-Lys-Asp-His-Asp-Ile-Asp-Tyr-Lys-Asp-Asp-Asp-Asp-Lys (SEQ ID NO: 17); antibodies having specificity for this sequence are sold by Sigma-Aldrich (St. Louis, Mo.). Thus, in one embodiment, the carrier comprises immobilized antibodies which have specificity for the DYKDDDDK (SEQ ID NO: 15) epitope; in another embodiment, the carrier comprises immobilized antibodies which have specificity for the DLYDDDDK (SEQ ID NO: 16) epitope. In another embodiment, the carrier comprises immobilized antibodies which have specificity for SEQ ID NO: 17. For example, in one embodiment, the ANTI-FLAG® M1, M2, or M5 antibody is immobilized on the interior surface of a column, or a portion thereof, and/or a bead or other support within a column.

After the recombinant polypeptides, proteins and protein fragments are separated from other components of the liquid mixture, the conditions in the column may be changed to release the bound material. For example, the bound molecules may be eluted by pH change, imidazole, or competition with another linker peptide from the column.

Alternatively, the target polypeptide, protein or protein fragment portion of the bound recombinant polypeptide, protein or protein fragment may be selectively released from immobilized metal. For example, if there is a cleavage site between the target polypeptide, protein or protein fragment and the metal ion-affinity peptide, and if the bound recombinant polypeptide, protein or protein fragment is treated with the appropriate enzyme, the target polypeptide, protein or protein fragment may be selectively released while the metal ion-affinity polypeptide fragment remains bound to the immobilized metal. For this purpose, the cleavage is preferably an enzymatically cleavable linker peptide having the ability to undergo site-specific proteolysis. Suitable cleaving enzymes in accordance with this invention are activated factor X (factor Xa), DPP I, DPP II, DPP IV, carboxylpeptidase A, collagen, enterokinase, human renin, thrombin, trypsin, ubtilisn and V5.

It is to be appreciated that some polypeptide or protein molecules will possess the desired enzymatic or biological activity with the metal chelate peptide still attached either at the C-terminal end or at the N-terminal end or both. In those cases the purification of the chimeric protein will be accomplished without subjecting the protein to site-specific proteolysis.

The present invention may be used to purify any prokaryotic or eukaryotic protein that can be expressed as the product of recombinant DNA technology in a transformed host cell. These recombinant protein products include hormones, receptors, enzymes, storage proteins, blood proteins, mutant proteins produced by protein engineering techniques, or synthetic proteins. The purification process of the present invention can be used batchwise or in continuously run columns.

It is to be understood that the present invention has been described in detail by way of illustration and example in order to acquaint others skilled in the art with the invention, its principles, and its practical application. Further, the specific embodiments of the present invention as set forth are not intended to be exhaustive or to limit the invention, and that many alternatives, modifications, and variations will be apparent to those skilled in the art in light of the foregoing examples and detailed description. Accordingly, this invention is intended to embrace all such alternatives, modifications, and variations that fall within the spirit and scope of the following claims. While some of the examples and descriptions above include some conclusions about the way the invention may function, the inventors do not intend to be bound by those conclusions and functions, but put them forth only as possible explanations in light of current understanding.

Abbreviations and Definitions

To facilitate understanding of the invention, a number of terms are defined below. Definitions of certain terms are included here. Any term not defined is understood to have the normal meaning used by scientists contemporaneous with the submission of this application.

The term "expression vector" as used herein refers to nucleic acid sequences containing a desired coding sequence and appropriate nucleic acid sequences necessary for the expression of the operably linked coding sequence in a particular host organism. Nucleic acid sequences necessary for expression in prokaryotes include a promoter, a ribosome binding site, an initiation codon, a stop codon, optionally an operator sequence and possibly other regulatory sequences. Eukaryotic cells utilize promoters, a Kozak sequence and often enhancers and polyadenlyation signals. Prokaryotic cells also utilize a Shine-Dalgarno Ribosome binding site. The present invention includes vectors or plasmids which can be used as vehicles to transform any viable host cell with the recombinant DNA expression vector.

"Operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to include promoters, enhancers, and other expression control elements (e.g., polyadenylation signals). Regulatory sequences include those that direct constitutive expression of a nucleotide sequence in many types of host cell and those that direct expression of the nucleotide sequence only in certain host cells (e.g., tissue-specific regulatory sequences).

The terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in laboratory manuals.

The term "hydrophilic" when used in reference to amino acids refers to those amino acids which have polar and/or charged side chains. Hydrophilic amino acids include lysine, arginine, histidine, aspartate (i.e., aspartic acid), glutamate (i.e., glutamic acid), serine, threonine, cysteine, tyrosine, asparagine and glutamine.

The term "hydrophobic" when used in reference to amino acids refers to those amino acids which have nonpolar side chains. Hydrophobic amino acids include valine, leucine, isoleucine, cysteine and methionine. Three hydrophobic amino acids have aromatic side chains. Accordingly, the term "aromatic" when used in reference to amino acids refers to the three aromatic hydrophobic amino acids phenylalanine, tyrosine and tryptophan.

The term "fusion protein" refers to polypeptides and proteins which consist of a metal ion-affinity linker peptide and a protein or polypeptide operably linked directly or indirectly to the metal ion-affinity peptide. The metal ion-affinity linker peptide may be located at the amino-terminal portion of the fusion protein or at the carboxy-terminal protein thus forming an "amino-terminal fusion protein" or a "carboxy-terminal fusion protein," respectively.

The terms "metal ion-affinity peptide", "metal binding peptide" and "linker peptide" are used interchangeably to refer to an amino acid sequence which displays an affinity to metal ions. The minimum length of the immobilized metal ion-affinity peptide according to the present invention is seven amino acids including four alternating histidines. The most preferred length is seven amino acids including four alternating histidines.

The term "enzyme" referred to herein in the context of a cleavage enzyme means a polypeptide or protein which recognizes a specific amino acid sequence in a polypeptide and cleaves the polypeptide at the scissile bond. In one embodiment of the present invention, enterokinase is the enzyme which is used to free the fusion protein from the immobilized metal ion column. In further embodiments, carboxylpeptidase A, DPP I, DPP II, DPP IV, factor Xa, human renin, TEV, thrombin or VIII protease is the enzyme.

The terms "cleavage site" used herein refers to an amino acid sequence which is recognized and cleaved by an enzyme or chemical means at the scissile bond.

The term "scissile bond" referred to herein is the juncture where cleavage occurs; for example the scissile bond recognized by enterokinase may be the bond following the sequence $(Asp_4)$-Lys in the spacer peptide or affinity peptide.

By the term "immobilized metal ion-affinity peptide" as used herein is meant an amino acid sequence that chelates immobilized divalent metal ions of metals selected from the group consisting of aluminum, cadmium, calcium, cobalt, copper, gallium, iron, nickel, ytterbium and zinc.

The term "capture ligand" means any ligand or receptor that can be immobilized or supported on a container or support and used to isolate a cellular component from cellular debris. Some non-limiting examples of capture ligands that may be used in connection with the present invention include: biotin, streptavidin, various metal chelate ions, antibodies, various charged particles such as those for use in ion exchange chromatography, various affinity chromatography supports, and various hydrophobic groups for use in hydrophobic chromatography.

For all the nucleotide and amino acid sequences disclosed herein, it is understood that equivalent nucleotides and amino acids can be substituted into the sequences without affecting the function of the sequences. Such substitutions is within the ability of a person of ordinary skill in the art.

The procedures disclosed herein which involve the molecular manipulation of nucleic acids are known to those skilled in the art.

EXAMPLE 1

Construction and Screening of a Metal Ion-Affinity Peptide Library

A pseudo-random glutathione-S-transferase C-terminal peptide library was constructed with the amino acid sequence of His-X-His-X-His-X-His where X is any amino acid except Gln, His and Pro. The library vector was constructed from the bacterial expression vector pGEX-2T. The library was constructed by annealing a pair of complimentary oligonucleotides together. Oligonucleotides were constructed as follows: 5'GATCCCATDNDCATDNDCATDNDCATTAA3' (SEQ ID NO: 18) and 5'AATTGTTAATGHNHATGH-NHATGHNHATGG3' (SEQ ID NO: 19) where D is nucleotides A, G, or T, H is nucleotides A, C, or T and N is nucleotides A, C, T, or G. The 5' end was phosphorylated with $T_4$ polynucleotide kinase and the oligonucleotides were annealed together to generate a cassette. The cassette was ligated into pGEX-2T, which had been digested with EcoRI and BamHI restriction endonucleases. Ligated vector was transformed into *E. coli* DH5-α using standard protocols. Transformants were plated on LB/ampicillin plates (100 mg/L) and incubated overnight at 37° C.

900 colonies were picked and placed on 9 master plates. Each master plate contained 100 colonies each and were grown overnight at 37° C. A piece of nitrocellulose was placed onto each of the master plates. This piece of nitrocellulose was then removed and the transferred colonies were placed onto a LB/ampicillin plate containing 1 mM isopropyl β-D-galactopyranoside (IPTG) to induce the expression of the GST fusion peptides. The cells were allowed to grow for an additional 4 hours at 37° C. The nitrocellulose filter was removed from the plate and placed sequentially on blotting paper containing the following solutions to lyse the cells in situ:

(a) 10% SDS for 10 minutes,
(b) 1.5 M sodium chloride, 0.5 M sodium hydroxide for 5 minutes
(c) 1.5 M sodium chloride, 0.5 M Tris-HCl pH 7.4 for 5 minutes
(d) 1.5 M sodium chloride, 0.5 M Tris-HCl pH 7.4 for 5 minutes
(e) 2×SSC for 15 minutes.

The filters were dried at ambient temperature followed by an incubation in Tris-buffered saline (TBS) containing 3% non-fat dry milk for 1 hour at room temperature. Filters were then washed 3×for 5 minutes with TBS containing 0.05% Tween-20 (TBS-T). To detect clones that were capable of binding to a metal ion, the filters were incubated with nickel NTA horseradish peroxidase (HRP) at a concentration of 1 mg/ml in TBS-T for 1 hour. The filters were then washed with TBS-T 3×for 5 minutes and incubated with 3-3'-5-5'-Tetramethylbenzidine (TMB) to detect the horseradish peroxidase. The reaction was stopped by placing the filters in water. 250 colonies, which were detected above, were picked from the master plate and placed into 1 ml of LB/ampicillin and grown overnight in a 96 deep well plate at 37° C. at 250 rpm on an orbital shaker. 10 μl of the overnight cultures were transferred to a fresh aliquot of LB/ampicillin (1 ml) in a 96 deep well plate and grown for an additional 3 hours. The culture was then induced by adding IPTG (final concentration of 1 mM) and the culture was allowed to grow for an additional 3 hours prior to harvesting by centrifugation. The media was decanted and the cells were frozen overnight at −20° C. in the collection plate. Cells were lysed with 0.6 ml of CelLytic-B (Sigma-Aldrich product no. B3553) and incubated for 15 minutes at room temperature. The cell debris was removed by centrifugation at 3,000×g for 15 minutes. Two experiments were done in parallel, one on a His-Select High Sensitivity (HS) nickel coated plate, and the second on HIS-Select High Capacity (HC) nickel coated plate. 0.1 ml of cell extracts of each clone were placed in a HS microwell plate in the presence of imidazole at a final concentration of 5 mM. This is the selective condition used for screening the different metal ion-affinity clones. HS plates were incubated for 4 hours at room temperature. Plates were then washed 3×with phosphate-buffered saline (PBS) containing 0.05% Tween 20 (PBS-T). The HS plates were then incubated with anti-GST at 1:1,000 dilution in PBS-BSA buffer (0.2 ml/well) for 1 hour at room temperature. HS plates were washed 3×with PBS-T. The HS plates were then incubated with anti-mouse HRP conjugate at 1:10,000 dilution in PBS-BSA buffer for 1 hour at room temperature. Plates were washed 3×with PBS-T. The plate was then developed with 2,2'azino-bis(3-ethylbenzthiazoline-6-sulfonic acid) ABST substrate. Color development was stopped by the addition of sodium azide to a final concentration of 2 mM. Absorbance of the plates was read at 405 nm using a Wallace 1420 plate reader. The HC plates were used to further analyze potential clones. To further characterize the clones, 0.2 ml of cell extracts were applied to the HC plates and the plates were incubated at ambient temperature for 1 hour. The plates were washed with PBS as described above. Twenty-one clones that produced the highest response on the HS plates were eluted from the corresponding HC plate. The selected cloned proteins were eluted from the HC plates by incubating at 37° C. for 15 minutes in 50 mM sodium phosphate, 0.3 M sodium chloride and 0.2 M imidazole buffer. Eluted proteins were then moved to clean tubes and analyzed by SDS-PAGE. All 21 clones had the expected molecular weight and were sequence verified.

These 21 colonies were grown overnight in 1 ml LB/ampicillin media at 37° C. at 250 rpm. 100 μl of the overnight cultures were transferred to 50 ml of fresh LB/ampicillin media and the cultures grown for an additional 3 hours at 37° C. The cultures were induced with IPTG (final concentration of 1 mM) and the cultures grown for an additional 3 hours prior to harvesting by centrifugation.

EXAMPLE 2

Construction of an N-Terminal Metal Ion-Affinity Fusion Protein

Two metal ion-affinity tags were introduced to the N-terminal of bacterial alkaline phosphatase (BAP). The constructs were constructed from the BAP expression vector pFLAG-CTS-BAP. Construction was done by annealing two pair of complimentary oligonucleotides together. The following oligonucleotides were constructed: 5'TATGCATAAT-CATCGACATGAACATA3' (SEQ ID NO: 20), 5'AGCTTAT-GTTTATGTCGATGATTATGCA3' (SEQ ID NO: 21), 5'TATGCATAAACATAGACATGGGCATA3' (SEQ ID NO: 22) and 5'AGCTTGATGCCCATGTCTATGTTTATGCA3' (SEQ ID NO: 23). The oligonucleotides were annealed together to generate a cassette. The cassette was ligated into pFLAG-CTS-BAP, which had been digested with NdeI and HindIII restriction endonucleases. Ligated vector was transformed into *E. coli* DH5-a using standard protocols and plated on LB/ampicillin.

EXAMPLE 3

Expression of an N-Terminal Metal Ion-Affinity Fusion Protein

MAT-BAP fusion peptide cultures were grown overnight in 1 ml LB/ampicillin at 37° C. 500 µl of overnight cultures were transferred to 500 ml of fresh TB media containing ampicillin (100 mg/L). The cultures were grown for three hours at 37° C. at 250 rpm. Protein expression was induced by the addition of IPTG (final concentration of 1 mM). Cultures were then grown for an additional three hours, harvested by centrifugation and stored at −70° C. until further use.

EXAMPLE 4

Metal Ion-Affinity Fusion Protein Purification Protocol #1

Cells were resuspended in 2 ml of TE (50 mM Tris-HCl pH 8.0, 2 mM EDTA). Lysozyme (4 mg/ml in 2 ml of TE) was added to the resuspended cells and the cells were lysed at ambient temperature for 4 hours. The cell debris was removed by centrifugation at 27,000×g for 15 minutes. The supernatant was dialyzed overnight against 50 mM Tris-HCl pH 8.0 to remove the EDTA. The dialyzed supernatant was applied to a 1 ml column containing a nickel biscarboxy-methyl-cysteine resin (nickel resin). The column was washed with 4 ml of 50 mM Tris-HCl pH 8.0 and then washed with 2 ml of 50 mM Tris-HCl pH 8.0, 10 mM imidazole. The column was then eluted 50 mM Tris-HCl pH 8.0 250 mM imidazole. Samples were analyzed for purity by SDS-PAGE.

EXAMPLE 5

Metal Ion-Affinity Fusion Protein Purification Protocol #2

Cells were resuspended with CelLytic B (Sigma-Aldrich product no. B3553), and 10 mM imidazole. The cells were solubilized by incubation for 15 minutes. The cell debris was removed by centrifugation at 15,000×g for 5 minutes at room temperature. A 0.5 ml column, containing nickel resin, was equilibrated with 10 column volumes (5 ml) of 50 mM sodium phosphate, pH 8, and 300 mM sodium chloride (column buffer). The supernatant was loaded on the column. The column was washed with 10 column volumes (5 ml) of 10 mM imidazole in column buffer. The column was eluted with 100 mM imidazole in column buffer. The samples were analyzed for specificity by SDS-PAGE.

EXAMPLE 6

Metal Ion-Affinity Fusion Protein Purification Protocol #3: Use of Chaotropic Agents The cells were resuspended in 100 mM sodium phosphate, pH 8, and 8 M urea (denaturant column buffer). The cells were solubilized by sonication three times, 15 seconds each, with a probe sonicator. Cell debris was removed by centrifugation at 15,000×g for 5 minutes at room temperature. A 0.5 ml column, containing nickel resin, was equilibrated with 10 column volumes (5 ml) of the denaturant column buffer. The supernatant was loaded on the column and the column was washed with 10 column volumes (5 ml) of denaturant column buffer. The column was sequentially eluted with 100 mM sodium phosphate, 8 M urea at pH 7.5, 7.0, 6.5, 6.0, 5.5, 5.0 and 4.5. The samples were analyzed for specificity by SDS-PAGE.

---

We claim:

1. A recombinant vector comprising a vector and a DNA sequence coding for a polypeptide, protein or protein fragment comprising the formula $R_1$-$Sp_1$-(His-$Z_1$-His-Arg-His-$Z_2$-His)-$Sp_2$-$R_2$, wherein (His-$Z_1$-His-Arg-His-$Z_2$-His) (SEQ ID NO: 24) is a metal ion-affinity peptide, $R_1$ is hydrogen, a polypeptide, protein or protein fragment, $Sp_1$ is a covalent bond or a spacer comprising at least one amino acid residue, $R_2$ is hydrogen, a polypeptide, protein or protein fragment, $Sp_2$ is a covalent bond or a spacer comprising at least one amino acid residue, $Z_1$ is an amino acid residue selected from the group consisting of Ala, Asn, Asp, Gln, Glu, Ile, Lys, Phe, Pro, Ser, Thr, Trp, and Val, and $Z_2$ is an amino acid residue selected from the group consisting of Ala, Asn, Asp, Cys, Gln, Glu, Gly, Ile, Leu, Lys, Met, Pro, Ser, Thr, Tyr, and Val, and wherein the recombinant vector is capable of directing expression of the DNA sequence in a compatible unicellular host organism.

2. The recombinant vector of claim 1, wherein $Z_1$ is Asn and $Z_2$ is Lys.

3. A host cell comprising the recombinant vector as set forth in claim 1.

4. The host cell of claim 3, wherein the recombinant vector comprises the DNA sequence wherein $Z_1$ is Lys and $Z_2$ is Gly.

5. The host cell of claim 4, wherein said host cell is *E. coli*, yeast, insect cells, mammalian cells, or plant.

6. The recombinant vector of claim 1, wherein $Sp^1$ or $Sp^2$ is a spacer comprising at least one amino acid residue, said spacer comprising an antigenic domain, wherein the antigenic domain comprises the formula

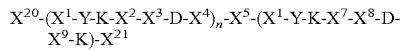

where:

D, Y and K are their representative amino acids;

$X^{20}$ and $X^{21}$ are independently a hydrogen or a covalent bond;

each $X^1$ and $X^4$ is independently a covalent bond or at least one amino acid residue selected from the group consisting of aromatic amino acid residues and hydrophilic amino acid residues;

each $X^2$, $X^3$, $X^7$ and $X^8$ is independently an amino acid residue selected from the group consisting of aromatic amino acid residues and hydrophilic amino acid residues;

$X^5$ is a covalent bond or a spacer domain, the spacer domain comprising at least one amino acid or a combination of multiple or alternating histidine residues, said combination comprising His-Gly-His, or -(His-X)$_m$-, wherein m is 1 to 6 and X is selected from the group consisting of Ala, Arg, Asn, Asp, Cys, Gln, Glu, Gly, His, Ile, Leu, Lys, Met, Phe, Pro, Ser, Thr, Trp, Tyr and Val;

$X^9$ is a covalent bond or an aspartate residue; and n is 0, 1 or 2.

7. The recombinant vector of claim 1, wherein $Sp^1$ or $Sp^2$ is a spacer comprising at least one amino acid residue, said spacer comprising an antigenic domain, wherein the antigenic domain comprises the formula

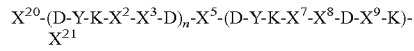

where:

D, Y, K are their representative amino acids;

$X^{20}$ and $X^{21}$ are independently a hydrogen or a covalent bond;

each $X^2$, $X^3$, $X^7$ and $X^8$ is independently an amino acid residue selected from the group consisting of aromatic amino acid residues and hydrophilic amino acid residues;

$X^5$ is a covalent bond or a spacer domain, the spacer domain comprising at least one amino acid or a combination of multiple or alternating histidine residues, said combination comprising His-Gly-His, or -(His-X)$_m$-, wherein m is 1 to 6 and X is selected from the group consisting of Ala, Arg, Asn, Asp, Cys, Gln, Glu, Gly, His, Ile, Leu, Lys, Met, Phe, Pro, Ser, Thr, Trp, Tyr and Val;

$X^9$ is a covalent bond or an aspartate residue; and n is at least 2.

8. The recombinant vector of claim 1, wherein $Sp^1$ or $Sp^2$ is a spacer comprising at least one amino acid residue, said spacer comprising an antigenic domain, wherein the antigenic domain comprises the formula

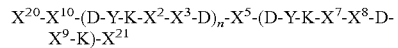

where:

D, Y, and K are their representative amino acids;

$X^{20}$ and $X^{21}$ are independently a hydrogen or a covalent bond;

$X^{10}$ is a covalent bond or an amino acid;

each $X^2$, $X^3$, $X^7$ and $X^8$ is independently an amino acid residue selected from the group consisting of aromatic amino acid residues and hydrophilic amino acid residues;

$X^5$ is a covalent bond or a spacer domain, the spacer domain comprising at least one amino acid or a combination of multiple or alternating histidine residues, said combination comprising His-Gly-His, or -(His-X)$_m$-, wherein m is 1 to 6 and X is selected from the group consisting of Ala, Arg, Asn, Asp, Cys, Gln, Glu, Gly, His, Ile, Leu, Lys, Met, Phe, Pro, Ser, Thr, Trp, Tyr and Val;

X⁹ is a covalent bond or an aspartate residue; and
n is at least 2.

9. The recombinant vector of claim 8, wherein the antigenic domain comprises the sequence Met-Asp-Tyr-Lys-Asp-His-Asp-Gly-Asp-Tyr-Lys-Asp-His-Asp-Ile-Asp-Tyr-Lys-Asp-Asp-Asp-Asp-Lys (SEQ ID NO: 17).

10. The recombinant vector of claim 1, wherein $Sp^1$ or $Sp^2$ is a spacer comprising at least one amino acid residue, said spacer comprising an antigenic domain, wherein the antigenic domain comprises the formula

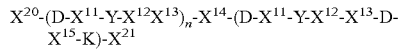

$$X^{20}\text{-}(D\text{-}X^{11}\text{-}Y\text{-}X^{12}X^{13})_n\text{-}X^{14}\text{-}(D\text{-}X^{11}\text{-}Y\text{-}X^{12}\text{-}X^{13}\text{-}D\text{-}X^{15}\text{-}K)\text{-}X^{21}$$

where:
D, Y and K are their representative amino acids;
$X^{20}$ and $X^{21}$ are independently a hydrogen or a covalent bond;
each $X^{11}$ is a covalent bond or an amino acid;
each $X^{12}$ is an amino acid selected from the group consisting of aromatic amino acid residues and hydrophilic amino acid residues;
each $X^{13}$ is a covalent bond or at least one amino acid selected from the group consisting of aromatic amino acid residues and hydrophilic amino acid residues;
$X^{14}$ is a covalent bond or a spacer domain, the spacer domain comprising at least one amino acid or a combination of multiple or alternating histidine residues, said combination comprising His-Gly-His, or -(His-X)$_m$-, wherein m is 1 to 6 and X is selected from the group consisting of Ala, Arg, Asn, Asp, Cys, Gln, Glu, Gly, His, Ile, Leu, Lys, Met, Phe, Pro, Ser, Thr, Trp, Tyr and Val;
$X^{15}$ is a covalent bond or an aspartate residue; and
n is 0 or at least 1.

11. The recombinant vector of claim 1, wherein $Sp^1$ or $Sp^2$ is a spacer comprising at least one amino acid residue, said spacer comprising an antigenic domain, wherein the antigenic domain comprises the sequence DYKDDDDK (SEQ ID NO: 15).

12. The recombinant vector of claim 1, wherein $Sp^1$ or $Sp^2$ is a spacer comprising at least one amino acid residue, said spacer comprising an antigenic domain, wherein the antigenic domain comprises the sequence DLYDDDDK (SEQ ID NO: 16).

13. A host cell comprising the recombinant vector as set forth in claim 6.

14. A host cell comprising the recombinant vector as set forth in claim 7.

15. A host cell comprising the recombinant vector as set forth in claim 8.

16. A host cell comprising the recombinant vector as set forth in claim 10.

17. The recombinant vector of claim 1 wherein $Z_1$ is selected from the group consisting of Ala, Asn, Ile, Lys, Phe, Ser, Thr, and Val, and $Z_2$ is selected from the group consisting of Ala, Asn, Gly, Lys, Ser, Thr, and Tyr.

18. The host cell of claim 3, wherein the recombinant vector comprises the DNA sequence wherein $Z_1$ is selected from the group consisting of Ala, Asn, Ile, Lys, Phe, Ser, Thr, and Val, and $Z_2$ is selected from the group consisting of Ala, Asn, Gly, Lys, Ser, Thr, and Tyr.

19. The recombinant vector of claim 6, wherein $Z_1$ is selected from the group consisting of Ala, Asn, Ile, Lys, Phe, Ser, Thr, and Val, and $Z_2$ is selected from the group consisting of Ala, Asn, Gly, Lys, Ser, Thr, and Tyr.

20. The recombinant vector of claim 7, wherein $Z_1$ is selected from the group consisting of Ala, Asn, Ile, Lys, Phe, Ser, Thr, and Val, and $Z_2$ is selected from the group consisting of Ala, Asn, Gly, Lys, Ser, Thr, and Tyr.

21. The recombinant vector of claim 8, wherein $Z_1$ is selected from the group consisting of Ala, Asn, Ile, Lys, Phe, Ser, Thr, and Val, and $Z_2$ is selected from the group consisting of Ala, Asn, Gly, Lys, Ser, Thr, and Tyr.

22. The recombinant vector of claim 10, wherein $Z_1$ is selected from the group consisting of Ala, Asn, Ile, Lys, Phe, Ser, Thr, and Val, and $Z_2$ is selected from the group consisting of Ala, Asn, Gly, Lys, Ser, Thr, and Tyr.

23. The recombinant vector of claim 19 wherein $Z_1$ is selected from the group consisting of Asn and Lys and $Z_2$ is selected from the group consisting of Gly and Lys.

24. The recombinant vector of claim 20 wherein $Z_1$ is selected from the group consisting of Asn and Lys and $Z_2$ is selected from the group consisting of Gly and Lys.

25. The recombinant vector of claim 21 wherein $Z_1$ is selected from the group consisting of Asn and Lys and $Z_2$ is selected from the group consisting of Gly and Lys.

26. The recombinant vector of claim 22 wherein $Z_1$ is selected from the group consisting of Asn and Lys and $Z_2$ is selected from the group consisting of Gly and Lys.

27. The recombinant vector of claim 19 wherein $Z_1$ is Asn and $Z_2$ is Lys.

28. The recombinant vector of claim 20 wherein $Z_1$ is Asn and $Z_2$ is Lys.

29. The recombinant vector of claim 21 wherein $Z_1$ is Asn and $Z_2$ is Lys.

30. The recombinant vector of claim 22 wherein $Z_1$ is Asn and $Z_2$ is Lys.

31. The host cell of claim 3, wherein the recombinant vector comprises the DNA sequence wherein $Z_1$ is Asn and $Z_2$ is Lys.

32. A process for producing a polypeptide, protein or protein fragment comprising the formula $R_1$-$Sp_1$-(His-$Z_1$-His-Arg-His-$Z_2$-His)-$Sp_2$-$R_2$, wherein (His-$Z_1$-His-Arg-His-$Z_2$-His) (SEQ ID NO: 24) is a metal ion-affinity peptide, $R_1$ is hydrogen, a polypeptide, protein or protein fragment, $Sp_1$ is a covalent bond or a spacer comprising at least one amino acid residue, $R_2$ is hydrogen, a polypeptide, protein or protein fragment, $Sp_2$ is a covalent bond or a spacer comprising at least one amino acid residue, $Z_1$ is an amino acid residue selected from the group consisting of Ala, Asn, Asp, Gln, Glu, Ile, Lys, Phe, Pro, Ser, Thr, Trp, and Val, and $Z_2$ is an amino acid residue selected from the group consisting of Ala, Asn, Asp, Cys, Gln, Glu, Gly, Ile, Leu, Lys, Met, Pro, Ser, Thr, Tyr, and Val, the process comprising (a) transforming a host cell with a recombinant vector encoding the polypeptide, protein or protein fragment comprising the formula $R_1$-$Sp_1$-(His-$Z_1$-His-Arg-His-$Z_2$-His)-$Sp_2$-$R_2$;

(b) culturing the host cell under conditions which permit the expression of the polypeptide, protein or protein fragment;

(c) lysing the host cell; and (d) purifying the polypeptide, protein or protein fragment or a portion thereof by metal ion affinity chromatography.

33. The process of claim 32, wherein the recombinant vector comprises a DNA sequence coding for the polypeptide, protein or protein fragment, wherein the recombinant vector is capable of directing expression of the DNA sequence in a compatible host cell.

34. The process of claim 33, wherein the recombinant vector comprises the DNA sequence wherein $Z_1$ is Asn and $Z_2$ is Lys or wherein $Z_1$ is Lys and $Z_2$ is Gly.

35. The process of claim 34, wherein the host cell is *E. coli*, yeast, insect cells, mammalian cells, or plants.

36. The process of claim 32, wherein $Z_1$ is selected from the group consisting of Ala, Asn, Ile, Lys, Phe, Ser, Thr, and Val, and $Z_2$ is selected from the group consisting of Ala, Asn, Gly, Lys, Ser, Thr, and Tyr.

* * * * *